United States Patent [19]

Shaknovich

[11] Patent Number: 5,669,924
[45] Date of Patent: Sep. 23, 1997

[54] Y-SHUTTLE STENT ASSEMBLY FOR BIFURCATING VESSELS AND METHOD OF USING THE SAME

[76] Inventor: Alexander Shaknovich, 1349 Lexington Ave., New York, N.Y. 10128

[21] Appl. No.: 548,459

[22] Filed: Oct. 26, 1995

[51] Int. Cl.$^6$ .................................................. A61F 2/06
[52] U.S. Cl. ................. 606/108; 606/198; 623/1; 623/12; 604/101
[58] Field of Search .................. 606/108, 195, 606/194, 198; 604/101, 284; 623/1, 12

[56] References Cited

U.S. PATENT DOCUMENTS

| | | |
|---|---|---|
| 2,624,341 | 1/1953 | Wallace .................. 604/284 |
| 4,309,994 | 1/1982 | Grunwald ................ 604/284 X |
| 4,390,599 | 6/1983 | Broyles . |
| 4,503,599 | 3/1985 | Dotter . |
| 4,580,568 | 4/1986 | Gianturco . |
| 4,655,771 | 4/1987 | Wallsten . |
| 4,665,918 | 5/1987 | Garza et al. . |
| 4,723,549 | 2/1988 | Wholey et al. ........... 604/101 X |
| 4,733,665 | 3/1988 | Palmaz . |
| 4,739,762 | 4/1988 | Palmaz . |
| 4,762,128 | 8/1988 | Rosenbluth . |
| 4,776,337 | 10/1988 | Palmaz . |
| 4,794,928 | 1/1989 | Kletschka ............... 604/101 X |
| 4,795,458 | 1/1989 | Regan . |
| 4,830,003 | 5/1989 | Wolff et al. . |
| 4,886,062 | 12/1989 | Wiktor . |
| 4,922,905 | 5/1990 | Strecker . |
| 4,950,227 | 8/1990 | Savin et al. . |
| 4,969,458 | 11/1990 | Wiktor . |
| 4,994,071 | 2/1991 | MacGregor .............. 606/194 |
| 5,035,706 | 7/1991 | Gianturco . |
| 5,037,427 | 8/1991 | Harada et al. . |
| 5,059,211 | 10/1991 | Stack et al. . |
| 5,064,435 | 11/1991 | Porter . |
| 5,089,005 | 2/1992 | Harada . |
| 5,089,006 | 2/1992 | Stiles . |
| 5,102,417 | 4/1992 | Palmaz . |
| 5,147,370 | 9/1992 | McNamara et al. . |
| 5,147,385 | 9/1992 | Beck et al. . |
| 5,183,085 | 2/1993 | Timmermans . |
| 5,192,085 | 3/1993 | Hull . |

(List continued on next page.)

FOREIGN PATENT DOCUMENTS

| | | | |
|---|---|---|---|
| 694197 | 10/1979 | U.S.S.R. | ................ 606/195 |
| 9409845 | 5/1994 | WIPO . | |
| 9526777 | 10/1995 | WIPO . | |

OTHER PUBLICATIONS

Shaknovich and Schatz, Physician Guide: Palmz–Schatz™ balloon expandable stent for coronary use. ©1994 by Johnson & Johnson Interventional Systems Co.
Fischman et al., 1994, N. Engl. J. Med. 331: 496–501.
Serruys et al., 1994, N. Engl. J. Med. 331: 489–495.
Topol, 1994; N. Engl. J. Med. 331:539–541.
Dorros et al., 1993, Cathet. Cardiovasc. Diagn. 28: 80–82.
Hearn et al., 1993, Circulation 88: 2086–2096.
Hallisey et al., 1992, Curr. Opin. Radiol. 4: 7–12.
Rocchini et al., 1992, Pediatr. Cardiol. 13: 92–96.
Anderson et al., 1992, J. am. Coll. Cardiol. 19: 372–381.
Brown et al., 1992 Cathet. Cardiovasc. Diagn. 27: 82–85.
Yang et al., 1991, Nippon Acta Radiol. 51: 970–972.
Trent et al., 1990, J. Vasc. Surg. 11: 707–717.

*Primary Examiner*—Michael H. Thaler
*Attorney, Agent, or Firm*—Brumbaugh, Graves, Donohue & Raymond

[57] ABSTRACT

The present invention relates to a Y-shuttle stent delivery system to be used in the placement of one or more stents in a bifurcating vessel. In particular, the stent delivery system of the invention comprises a tubular stent delivery catheter (or "shuttle") having a Y-shaped bifurcated expandable deployment segment which may be inserted into both branches of a bifurcating vessel. One or more stents may be mounted, in a contracted conformation, on the deployment segment, and may be deployed in both branches of the vessel simultaneously by expanding the deployment segment by an ancillary means, such as one or more balloon catheters, positioned within the shuttle.

4 Claims, 22 Drawing Sheets

U.S. PATENT DOCUMENTS

| | | |
|---|---|---|
| 5,197,978 | 3/1993 | Hess . |
| 5,201,757 | 4/1993 | Heyn et al. . |
| 5,221,261 | 6/1993 | Termin et al. . |
| 5,224,953 | 7/1993 | Morgentaler . |
| 5,279,565 | 1/1994 | Klein et al. . |
| 5,282,824 | 2/1994 | Gianturco . |
| 5,304,121 | 4/1994 | Sahatjian . |
| 5,316,023 | 5/1994 | Palmaz et al. . |
| 5,330,500 | 7/1994 | Song . |
| 5,336,178 | 8/1994 | Kaplan et al. . |
| 5,360,443 | 11/1994 | Barone et al. . |
| 5,389,106 | 2/1995 | Tower . |
| 5,409,495 | 4/1995 | Osborn ................................ 604/101 X |

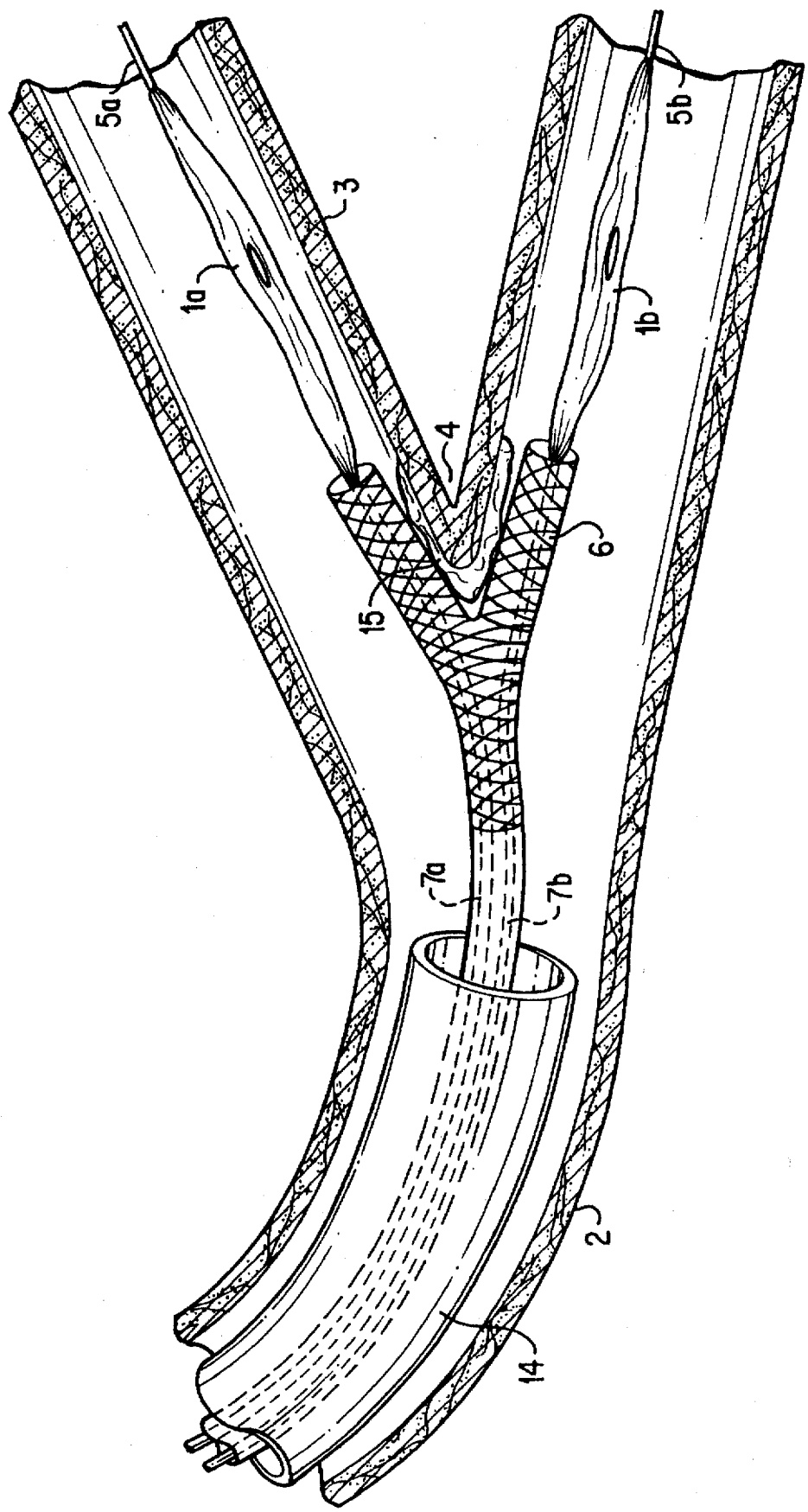

Y-SHUTTLE STENT ASSEMBLY FOR BIFURCATING VESSELS AND METHOD OF USING THE SAME

1. INTRODUCTION

The present invention relates to a shuttle stent delivery system to be used in the placement of one or more stents in a bifurcating vessel. In particular, the stent delivery system of the invention comprises a tubular stent delivery catheter (or "shuttle") having a Y-shaped bifurcated expandable deployment segment which may be inserted into both branches of a bifurcating vessel. One or more stents may be mounted, in contracted conformation, on the deployment segment, and may be deployed in both branches of the vessel simultaneously by expanding the Y-shaped deployment segment by an ancillary means, such as one or more balloon catheters, positioned within the shuttle.

2. BACKGROUND OF THE INVENTION

2.1. A History of Stent Development

Over the past fifteen years, the fields of interventional cardiology and interventional radiology have witnessed a number of paradigm shifts in the treatment of occluded (so called "stenotic") coronary arteries (among other blood vessels, various tubular conduits and similar structures). The earliest approach, still used for particular coronary applications, is by-pass surgery, which constructs a vascular detour around the occlusion.

Later, it was found that in certain patients, a much less invasive approach, which did not require thoracotomy, could be used. This technique, known as percutaneous transluminal coronary angioplasty ("PTCA"), introduces a catheter carrying a deflated balloon into a large artery in the leg or arm of a patient, threads the catheter into a partially occluded coronary artery, and then inflates the balloon to force open the obstruction. The balloon is then deflated, and the catheter withdrawn from the patient. PTCA has, however, two major shortcomings: first, in 3–5% of patients treated with PTCA, the treated coronary artery re-occludes within the first 24–48 hours after the procedure, despite the use of anticoagulant drugs to deter the reformation of the occlusion (called "abrupt closure"); second, in 30–50% of patients treated with PTCA, the subsequent healing process in the treated coronary artery is associated with sufficient recoil, scarring and/or proliferation of smooth muscle cells to cause re-occlusion of the artery (called "restenosis").

In hopes of preventing abrupt closure and restenosis, coronary artery stents were developed (Topol, 1994, N. Engl. J. Med. 331:539–541). Such stents are tubular devices which provide structural support for maintaining an open vessel. Recently, the placement of such stents has been found to be associated with better angiographic and clinical outcomes than PTCA (Serruys et al., 1994, N. Engl. J. Med. 331:489–495; Fischman et al., 1994, N. Engl. J. Med. 331:496–501), including a lower rate of restenosis. These benefits were achieved, however, at the price of significantly higher procedural costs related to intra- and post-procedural aspects of the stent procedure, and were associated with a significantly higher risk of vascular complications (such as hemorrhage) occurring at the percutaneous access site shortly after the stent procedure. The risk of vascular complications is associated with the aggressive anticoagulation regimen used to avoid thrombosis occurring in the stent itself. Modifications in the strategy of optimal stent placement ("deployment") have been introduced to minimize the risk of such complications.

Procedures used for stent deployment in a vessel generally involve the introduction of the stent, in a contracted condition, into the vessel, followed by the expansion of the stent such that it is locked in the desired position in apposition to the vessel wall. Certain stents require an ancillary means for expansion. For example, a stent may be fitted over a collapsed angioplasty balloon, which is then introduced into the vessel and inflated, thereby expanding the stent and deploying it in the desired location. Such stents are referred to as "non-self-expanding stents". Other stents are capable of expanding when released from the contracted condition (similar to the release of a compressed spring); such stents are referred to as "self-expanding stents".

The conventional implantation of non-self-expanding stents typically incorporates three distinct steps. First, where an obstruction narrows a vessel to an extent which precludes introduction of the stent delivery system, an adequate channel for passage of the balloon-stent assembly is created by inflating a balloon not carrying a stent within the stenosed region (hereafter referred to as pre-dilatation). In order to avoid excessive trauma to the target vessel, the balloon used for pre-dilatation is optimally of slightly smaller diameter than the vessel adjacent to the treatment site.

Second, the balloon-stent assembly is advanced into the desired location within the vessel and the stent is expanded by inflating the carrier balloon, so as to achieve contact between the stent and the walls of the vessel (deployment). In order to achieve sufficient expansion of the stent along its entire length and to anchor the stent in the target vessel, the balloon used for deployment is optimally, when inflated, of the same or slightly greater diameter than the vessel adjacent to the treatment site and of greater length than the stent.

Third, optimization of the axially symmetric tubular geometry of the stent and uniform circumferential contact of the stent with the walls of the vessel is achieved by inflating a balloon capable of withstanding high distending pressures within the deployed stent (hereafter referred to as post-dilatation). In order to avoid damage to the target vessel adjacent to the implanted stent, the balloon used for post-dilatation is optimally shorter than the stent. While the first and third of these three steps may occasionally be omitted, they are recommended for most stent placement applications.

For best results, the choice of balloon optimal for one of the foregoing three steps is typically not optimal for the other steps. However, as the number of balloon changes increases, the duration, difficulty and cost of the procedure also increases, as does the likelihood of hemorrhagic complications and infection.

2.2. The Shuttle Stent Delivery System

As described in pending U.S. patent application Ser. No. 08/430,378, the entirety of which is hereby incorporated herein by reference, a "shuttle" stent delivery system has been developed which provides the benefits of an optimal three-step stent placement procedure using multiple balloons, but which obviates the need for balloon exchanges. The system utilizes a tubular stent delivery catheter (hereafter referred to as a "shuttle") comprising a deployment segment having an expandable portion, onto which a stent may be mounted in a contracted conformation. Unlike previously known delivery catheters, however, the deployment segment is not expanded by means intrinsic to itself, but rather is expanded by ancillary means, for example, by a balloon catheter separate and distinct from the shuttle. Multiple balloon changes are rendered unnecessary because the structural design of the deployment segment supplies the optimal physical characteristics offered by multiple balloons.

In particular embodiments of the shuttle stent delivery system, the shuttle comprises a deployment segment having an expandable portion over which a stent is mounted in contracted condition. The stent-bearing expandable portion of the deployment segment is flanked by segments which are not expandable to the same degree as the stent-bearing portion. Optionally, the deployment segment comprises a releasable biological, pharmaceutical, or structural substance.

For stent placement in a partially occluded blood vessel (or similar structure) in a patient, a guide wire, having a length greater than the balloon catheter, may be introduced into the vessel. A shuttle with an expandable stent mechanically or by other means attached onto the deployment segment in contracted condition, may be mounted coaxially over the shaft of the balloon catheter outside the patient. The shuttle may be designed to be coaxially mounted over the shaft of the balloon catheter over the entire length of the shuttle (hereafter referred to as an "over the catheter" shuttle) or only over a distal segment of the shuttle comprising the deployment segment (hereafter referred to as a "monorail" shuttle). For the over-the catheter shuttle, the balloon catheter used has a length greater than the shuttle. The balloon catheter is designed such that the balloon is reliably and repeatedly capable of advancing in unexpanded (i.e., never inflated) or collapsed (i.e., inflated at least once and then deflated) condition through the entire length of the shuttle and in and out of the distal end of the stent shuttle.

The occluded region of the vessel may then be pre-dilated using the balloon catheter. Then, without withdrawing the balloon catheter from the patient, the balloon may be deflated and advanced beyond (distal to) the occlusion, and the shuttle, fitting over the shaft of the balloon catheter, may be positioned such that the stent-bearing deployment segment is positioned within the pre-dilated occluded portion of the vessel. The balloon may then be pulled back into the deployment segment of the shuttle, and expanded to high pressures. Expanding the balloon accomplishes deployment of the stent, and also offers the benefits of post-dilatation. The need for a separate, shorter, post-dilatation balloon should be obviated by the relatively non-expandable segments flanking the expandable region of the deployment segment, which protect the vessel adjacent to the stent from damage. Moreover, releasable substances comprised in the deployment segment may be liberated by the expansion of the deployment segment via inflation of the balloon. Following stent deployment, the balloon may be deflated and the stent delivery and balloon catheters may be removed from the patient.

The shuttle stent delivery system may be used for the placement of either non-self-expanding or self-expanding stents in blood vessels or similar structures. Moreover, the system may be used to deploy multiple stents in a single procedure, and may be used in conjunction with an embolic filter.

2.3. Special Problems Encountered when Treating Bifurcating Vessels

A blood vessel or similar conduit which, along its course, extends a major branch vessel, is termed a "bifurcating vessel". The structural point of bifurcation, where the main trunk vessel and its side branch vessel meet, is termed the origin of the side branch, and the structure forming the angle between the vessels is termed the "carina".

Lesions that involve both the main trunk vessel and the side branch vessel are termed "bifurcating" lesions. Such lesions in a bifurcating epicardial coronary artery, involving a major side branch, are quite common. Typically, the side branch itself may contain significant atherosclerotic disease at, or in proximity to, its origin. Even in cases where the side branch is free of significant lesions, interventional manipulation of the main trunk vessel often results in compromising the side branch by a dissection, thrombus or spasm, or by causing a shift in the position of an atherosclerotic plaque in the main trunk vessel which partially or completely occludes the origin of the side branch. Accordingly, optimal management of bifurcating lesions involves treatment of both the main trunk vessel across the origin of the side branch as well as the origin and/or proximal segment of the side branch.

Two strategies for the treatment of lesions in bifurcating vessels are currently in use, which involve either (i) sequential or (ii) simultaneous treatment of the main trunk vessel and its side branch vessel. Such treatment may involve PTCA, atherectomy, or stent placement.

Implementing the sequential treatment strategy generally involves, first, the introduction of a guidewire into the main trunk vessel and treatment of that vessel by PTCA, atherectomy, or stent placement. Then, the guidewire and any treatment catheter are withdrawn from the main trunk vessel, and a guide wire is passed into the side branch vessel, followed by treatment of the side branch vessel by PTCA, atherectomy, or stent placement. This sequential approach is associated with several problems.

First, after the initial manipulation of the main trunk vessel, it may be impossible for the operator to pass a guide wire into the side branch vessel because an occlusive or nearly-occlusive plaque, dissection, thrombus or spasm caused by the first procedure blocks access to the side branch vessel. "Protection" of the side branch vessel by placement of a second guide wire into the side branch vessel prior to the initial manipulation of the main trunk vessel is not possible with rotational atherectomy, because the burr operating in the main trunk vessel would almost certainly ablate and severely damage the second guide wire. Nor is such protection possible during stent placement, because the stent in the main trunk vessel could trap the second guide wire between the stent and the vessel wall and prevent its withdrawal from the patient. Even in directional atherectomy, the placement of a second guide wire in the side branch is technically difficult. In performing sequential PTCA, protection of the side branch vessel with a second guide wire is possible, but often results in a back-and-forth displacement of plaque into the vessel not being balloon dilated.

Simultaneous manipulation of the main trunk vessel across the origin of the side branch and of the origin of the side branch vessel over two separate guide wires (one in the main trunk vessel, another in the side branch vessel), is not possible with any of the currently available types of atherectomy catheters, but is possible during PTCA or stent placement. Management of bifurcating lesions with PTCA involves simultaneously inflated balloons. The simultaneously inflated balloons may be either overlapping or non-overlapping. Overlapping inflated balloons are referred to as "kissing" if the angle between the main trunk and the side branch is less than 90 degrees (FIG. 1), as is typical for most side branches of native coronary arteries, or "divorcing" if the angle between the main trunk and the side branch is greater than 90 degrees (FIG. 2), as is typical for lesions involving a distal anastomosis of a saphenous vein bypass graft and its target vessel.

So-called "overlapping" balloons are simultaneously inflated side by side. This configuration may risk significant disruption of the main trunk vessel proximal to the side branch if the diameter of the main trunk proximal to the origin of the side branch is less than the sum of the diameters of the proximal side branch vessel and the main trunk vessel distal to the side branch origin.

If it is not safe to inflate two balloons simultaneously in the overlapping configuration, non-overlapping balloon placement may be attempted in one of two possible configurations, again depending on the relative size of the main trunk, proximal and distal to the branch origin, and the size of the branch itself.

One non-overlapping balloon configuration places one balloon entirely in the side branch, as close to the branch origin as possible without protruding into the main trunk, with the second balloon in the main trunk extending across the origin of the side branch (FIG. 3).

A second non-overlapping balloon configuration places a balloon entirely in the main trunk distal to, but as close as possible to, the origin of the side branch without protruding across it, with the second balloon in the side branch extending across its origin into the more proximal main trunk (FIG. 4).

Both of the foregoing non-overlapping balloon placement strategies are associated with balloon slippage during inflation and may be suboptimal for the treatment of rigid lesions or lesions prone to recoil. Moreover, any balloon-based strategy for management of bifurcating lesions has all the shortcomings of PTCA, namely, significant recoil at the treatment sites, an approximately 5% risk of abrupt closure of one of the vessels treated, and an approximately 40–50% rate of restenosis.

Several stent-based strategies for management of bifurcating lesions are possible with currently available stents and stent delivery systems. All typically involve pre-dilatation of the main trunk vessel and the side branch vessel, prior to stent placement, if the lumen of either vessel is initially not sufficient for stent delivery and/or for assessment of target site distensibility by balloons. Such strategies may involve either sequential or simultaneous deployment of, alternatively, over-lapping or non-overlapping stents.

Conventional sequential stent placement strategies require removal of any second "protection" guide wire prior to the placement of the first stent, in order to avoid trapping of the guide wire. There are two distinct stent placement configurations which may be used. The first stent may be placed entirely in the side branch vessel, as close to the origin as possible without protruding into the main trunk vessel, after which the second stent may be placed in the main trunk vessel extending across the origin of the side branch vessel (FIG. 5). Alternatively, the first stent may be placed entirely in the main trunk vessel distal to but as close as possible to the origin of the side branch vessel without protruding across it, after which the second stent may be placed in the side branch vessel extending across its origin into the more proximal main trunk vessel (FIG. 6).

Either of these sequential non-overlapping stent placement strategies may become impossible to complete if the first stent is placed too proximally, such that it obstructs the path required for placement of the second stent. In addition, such strategies may, consequent to optimal placement of the stents, preclude subsequent balloon catheter access and intravascular ultrasound assessment of one or more distal limbs arising beyond the original point of bifurcation, and may produce a suboptimal result if the first stent is placed too distally.

Sequential overlapping stent placement strategies involve placement of the first stent across the origin of the side branch vessel (FIG. 7) or across the continuation of the main trunk vessel distal to the side branch (FIG. 8), re-positioning the guide wire through the stent into the unstented distal limb of the bifurcation, and then placement of the second stent through the first stent across the bifurcation.

Either sequential overlapping stent placement strategy may become impossible to perform if the first stent cannot be recrossed with a guide wire or with the second stent. Further, the implementation of such strategies is likely to result in distortion of the optimal geometry of both stents, and will in most cases preclude catheter access to and intravascular ultrasound assessment of both distal limbs of the bifurcation.

Simultaneous stent placement strategies permit protection of the side branch throughout the procedure but require simultaneous overlapping stent placement (FIG. 9), because of concerns regarding trapping of one of the delivery systems by the other stent with any attempted simultaneous non-overlapping deployment (FIGS. 10 and 11).

Essentially, simultaneous overlapping stent placement creates a more proximal carina for the treated bifurcation. Stent-bearing deployment balloons are placed side by side in the main trunk vessel proximal to the side branch, and are simultaneously inflated (FIG. 9). As discussed above, this strategy may risk disruption of the main trunk vessel proximal to the origin of the side branch if the diameter of the main trunk vessel proximal to the origin of the side branch is significantly less than the sum of the diameters of the two stent delivery balloons matched to the distal limbs of the bifurcation. This risk is particularly significant in view of high-pressure deployment strategies currently in favor. Nonetheless, properly executed simultaneous overlapping stent placement is the preferred strategy for catheter-based management of bifurcating lesions because it offers the best prospects for lack of distortion of the optimal geometry of both stents, and because it may, in most cases, permit subsequent catheter access to, and intravascular ultrasound assessment of, both distal limbs of the bifurcation.

Currently, simultaneous overlapping stent placement is practiced by hand-crimping commercially available Palmaz-Schatz stents (see U.S. Pat. No. 4,733,665 by Palmaz) on PTCA balloons. Protective stent delivery sheaths (including commercially available integrated stent delivery systems) cannot be used because of their large size. Mounting a stent directly on the balloon by hand-crimping may inadvertently result in damage to the delivery balloon. Such damage may only become apparent during attempted stent deployment and may result in incomplete stent expansion and/or an inability to retract the stent and/or damaged balloon from the target vessel. Moreover, simultaneous inflation of two delivery balloons side by side may result in flaring of the edges of one stent, which may then puncture the other delivery balloon, potentially leading to incomplete stent expansion and difficulty in withdrawing the stent and/or balloon out of the target vessel. Delivery of two unsheathed hand-crimped stents may further result in slippage and/or embolization of one or both stents. Finally, the overlapping proximal segments of the two stents offer only partial protection against disruption of the main trunk vessel proximal to the bifurcation during simultaneous inflation of the deployment balloons. These balloons generally extend proximally beyond the proximal margins of the stents. Because the diameter of the main trunk vessel proximal to the origin of the side branch is typically less than the sum of the diameters of the two stent delivery systems, simultaneous inflation of the side-by-side balloons risks disruption of the main vessel.

There is, therefore, a need for an improved delivery system for the placement of stents in bifurcating vessels which avoids some or all of the pitfalls of presently used methods.

3. SUMMARY OF THE INVENTION

The present invention relates to a shuttle stent delivery system to be used in the placement of one or more stents in a bifurcating vessel. In particular, the stent delivery system of the invention comprises a tubular stent delivery catheter having a distal bifurcated expandable deployment segment which may be inserted into both branches of a bifurcated vessel; because the deployment segment has a shape similar to the letter "Y", the stent delivery catheter is hereafter referred to as the "Y-shuttle". One or more stents may be mounted, in a contracted conformation, on the deployment segment, and may be deployed in both branches of the bifurcating vessel simultaneously by expanding the deployment segment by an ancillary means, such as one or more balloon catheters, positioned within the shuttle.

The Y-shuttle offers numerous advantages over previously available stent placement systems. By enabling simultaneous stent deployment, the Y-shuttle avoids the difficulties encountered in sequential placement strategies, wherein deployment of a first stent may interfere with placement of a second stent, or distortion of stent geometry may occur. Furthermore, the Y-shuttle system circumvents the risk of trapping interventional elements associated with simultaneous placement of non-overlapping stents and protects the main trunk proximal to the branch origin against damage associated with simultaneous overlapping stent placement. In addition, because stents are mounted on the Y-shuttle rather than one or more balloons, the present invention avoids damage to the balloon, incomplete stent expansion, and difficulties in retrieving elements of the delivery system from the patient.

4. BRIEF DESCRIPTION OF THE FIGURES

FIG. 1. Simultaneously inflated PTCA balloons (1a and 1b), in "kissing" orientation, in a main trunk vessel (2) and its side branch vessel (3).

FIG. 2. Simultaneously inflated PTCA balloons (1a and 1b), in "divorcing" orientation, in a main trunk vessel (2) and its side branch vessel (3).

FIG. 3. Overlapping balloon configuration having one balloon (1a) entirely in the side branch vessel (3), as close to the branch origin (4) as possible without protruding into the main trunk vessel (2), with the second balloon (1b) in the main trunk extending across the origin of the side branch.

FIG. 4. Non-overlapping balloon configuration having a balloon (1a) entirely in the main trunk vessel (2) distal to, but as close as possible to, the origin (4) of the side branch without protruding across it, with the second balloon (1b) in the side branch vessel (3) extending across its origin (4) into the more proximal main trunk vessel.

FIG. 5. Sequential non-overlapping stent placement strategy in which (A) a guide wire (5) is passed into the side branch vessel (3), and (B) a first stent (6a) is placed entirely in the side branch vessel as close to the origin (4) as possible without protruding into the main trunk vessel (2), after which (C) a guide wire is passed into the main trunk vessel and (D) a second stent (6b) is placed in the main trunk vessel extending across the origin of the side branch vessel.

FIG. 6. Sequential non-overlapping stent placement strategy in which (A) a guide wire (5) is passed into the main trunk vessel (2) and (B) a first stent (6a) is placed entirely in the main trunk vessel distal to but as close as possible to the origin (4) of the side branch vessel (3) without protruding across it, after which (C) a guide wire is passed into the side branch vessel and (D) a second stent (6b) is placed in the side branch vessel extending across its origin into the more proximal main trunk vessel.

FIG. 7. Sequential overlapping stent placement strategy in which (A) a guide wire (5) is passed into the main trunk vessel (2) and (B) a first stent (6a) is placed in the main trunk vessel across the origin (4) of the side branch vessel (3), (C) the guide wire is re-positioned through the stent into the side branch vessel, and (D) a second stent (6b) is placed through the first stent across the bifurcation.

FIG. 8. Sequential overlapping stent placement strategy in which (A) a guide wire (5) is passed into the side branch vessel (3) and (B) a first stent (6a) is placed in the side branch vessel across the origin (4) and into the main trunk vessel (2), (C) the guide wire is re-positioned through the stent into the main trunk vessel, and (D) a second stent (6b) is placed through the first stent across the bifurcation.

FIG. 9. Simultaneous overlapping stent placement, wherein guidewires (5a and 5b) have been inserted, respectively, into the main trunk vessel (2) and the side branch vessel (3), over which stents (6a and 6b), mounted on balloon catheters (1a and 1b) have been introduced. The balloons are inflated simultaneously to deploy the stents.

FIG. 10. An undesirable consequence of simultaneous non-overlapping stent deployment, wherein the shaft of a balloon catheter (7), used to deploy a stent (6a; expanded by balloon 1a) in the main trunk vessel (2) distal to the origin (4) of the side branch vessel (3), is trapped by a simultaneously deployed non-overlapping stent (6b; expanded by balloon 1b) crossing the origin and extending into the side branch vessel.

FIG. 11. An undesirable consequence of simultaneous non-overlapping stent deployment, wherein the shaft of a balloon catheter (7), used to deploy a stent (6a; expanded by balloon 1a) in the side branch vessel (3), is trapped by a simultaneously deployed non-overlapping stent (6b; expanded by balloon 1b) in the main trunk vessel (2) which crosses the origin (4).

FIG. 12. (A) Y-shuttle deployment segment. (B–E) Y-shuttle deployment segments with stents (6) mounted in various configurations.

FIG. 13. Y-shuttle deployment segment within a guiding catheter.

FIG. 14. (A) Pre-dilatation of a partially occluded bifurcating vessel, followed by (B) deflation and advancement of the balloons distal to the lesion.

FIG. 15. Stent positioning following pre-dilatation.

FIG. 16. Withdrawal of the balloons into the deployment segment.

FIG. 17. Stent deployment.

FIG. 18. Reverse-tapered balloon.

FIG. 19. (A) Conventional PTCA balloons in "kissing" configuration in Y-shaped deployment segment within a bifurcating vessel, showing distortion of the main trunk vessel. (B) Reverse-tapered balloons in "kissing" configuration in Y-shaped deployment segment within a bifurcating vessel.

5. DETAILED DESCRIPTION OF THE INVENTION

Stent delivery systems of the invention share the common feature of a Y-shuttle having a Y-shaped stent deployment segment which is expanded by a means ancillary to the delivery catheter, such as by one or more balloon catheters.

Such systems may be better understood by reference to FIGS. 12–19, which illustrate nonlimiting embodiments of the invention.

FIG. 12A depicts a Y-shuttle deployment segment having a trunk (8), a hinge region (9), a carina (11) and two arms (10). FIG. 12B depicts one embodiment of the Y-shuttle deployment segment wherein one stent (6a) is mounted on the trunk (8) extending across the hinge region (9) into one arm (10a), and a second stent (6b) is mounted on the other arm (10b) of the deployment segment. FIG. 12C depicts the same positioning of stents as in FIG. 12B, except that the expandable areas on which the stents are mounted (12a and 12b) are surrounded by less expandable flanking regions (13a and 13b). FIG. 12D depicts a Y-shuttle deployment segment with stents (6a, 6b and 6c) mounted, respectively, on the trunk (8) and both arms (10a and 10b). FIG. 12E depicts a Y-shaped stent (6) mounted on the Y-shuttle deployment segment, with less-expandable flanks (13) bordering the expandable portion (12).

FIGS. 14–17 depict a general sequence of steps for stent placement according to the invention. The type of stent and balloons used, and other features of these illustrations, is by way of example only and is non-limiting as to the scope of the invention.

Figure 14A:
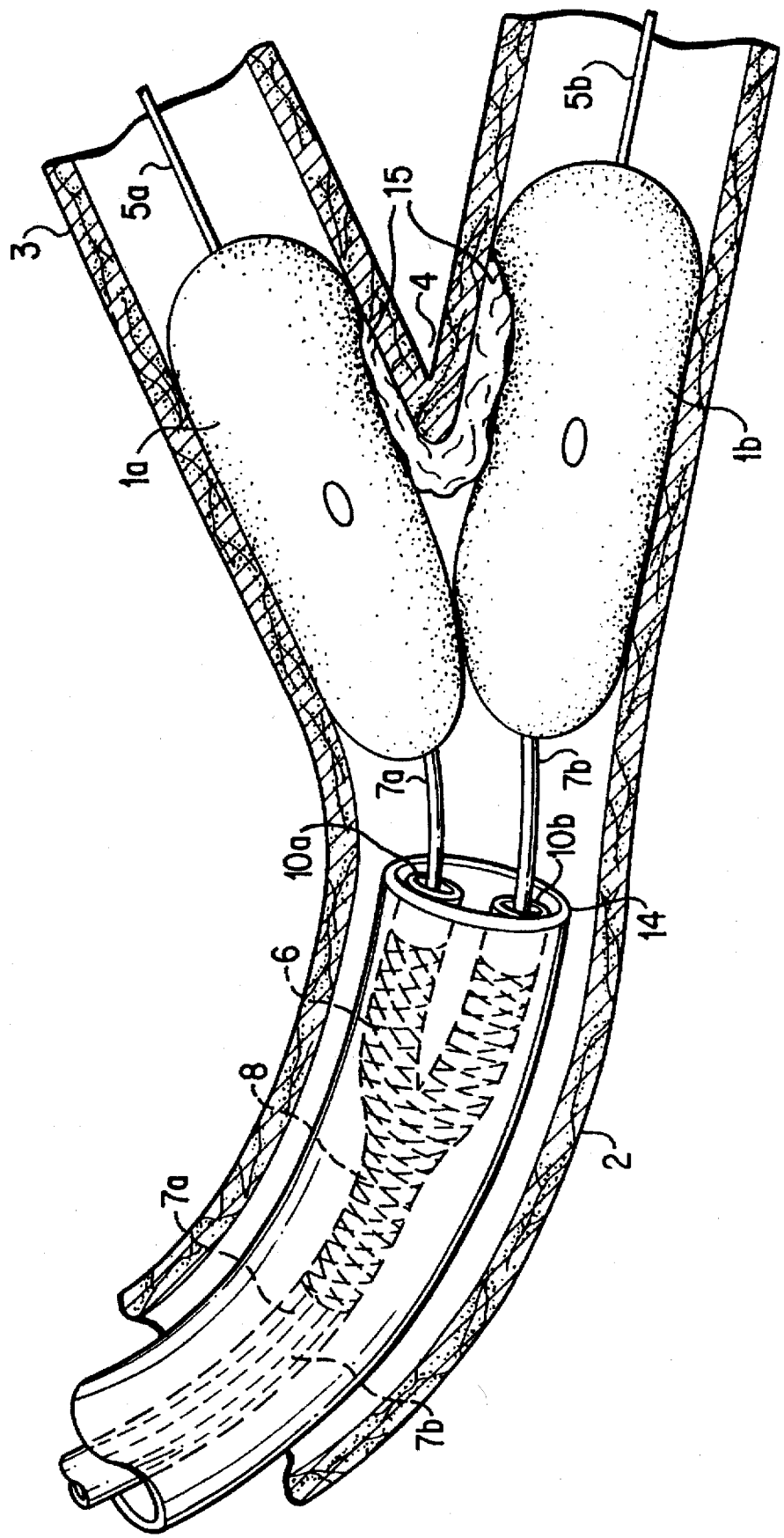
Figure 14B:
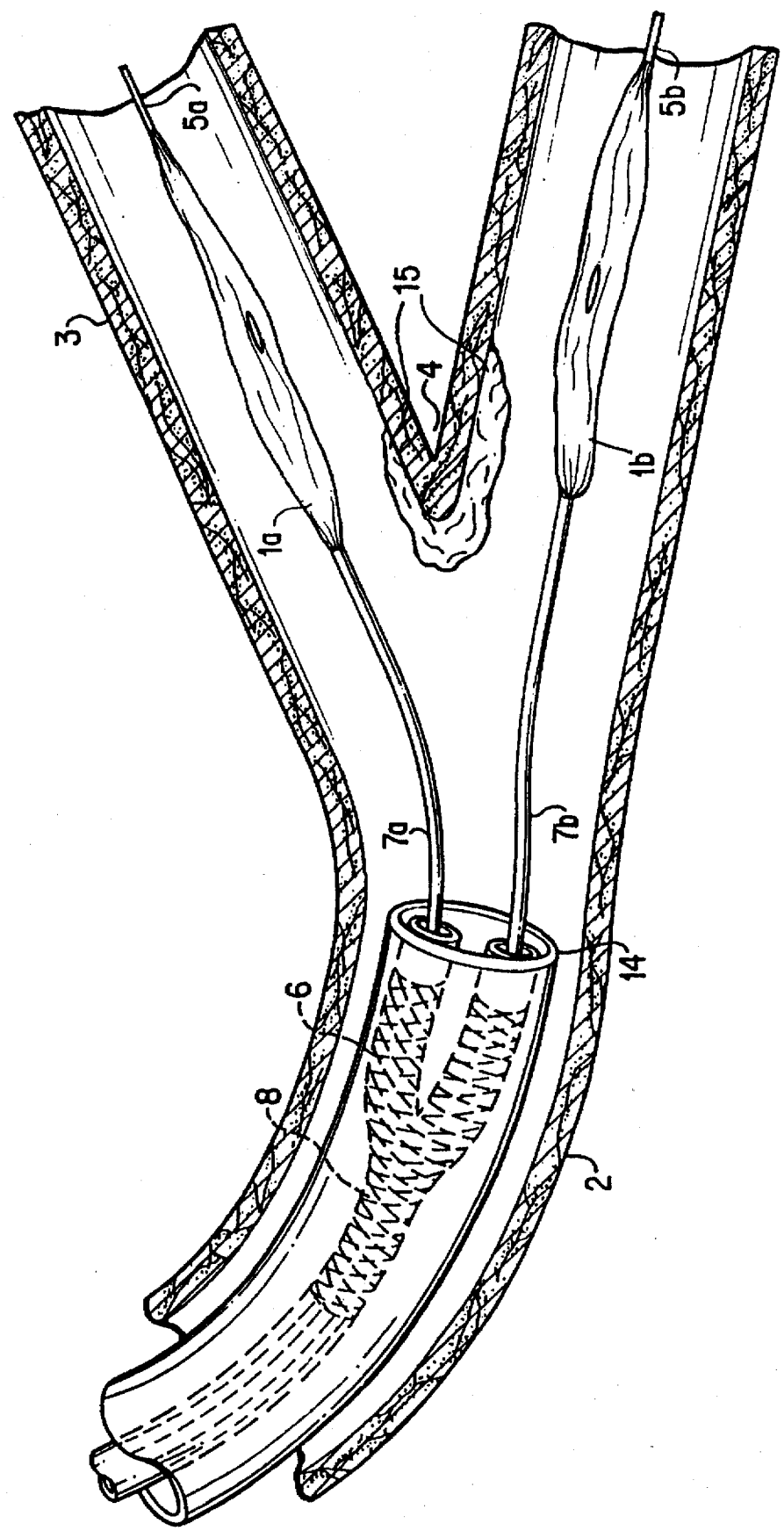

FIG. 14A depicts a bifurcating blood vessel consisting of a main trunk vessel (2) and its side branch (3), with a bifurcating atherosclerotic lesion (15) at the carina. The Y-shuttle, in a guiding catheter (14) has been introduced into the vessel and positioned proximal to the bifurcation. The Y-shuttle is mounted over the shafts of two balloon catheters (7a and 7b), which have been passed through the arms (10a and 10b) of the Y-shaped deployment segment such that the balloons (1a and 1b) are positioned over the lesions. The balloons are inflated to pre-dilate the vessels prior to stent placement. In the next step of the procedure (FIG. 14B), the balloons have been deflated and advanced distal to the lesion.

Figure 16:
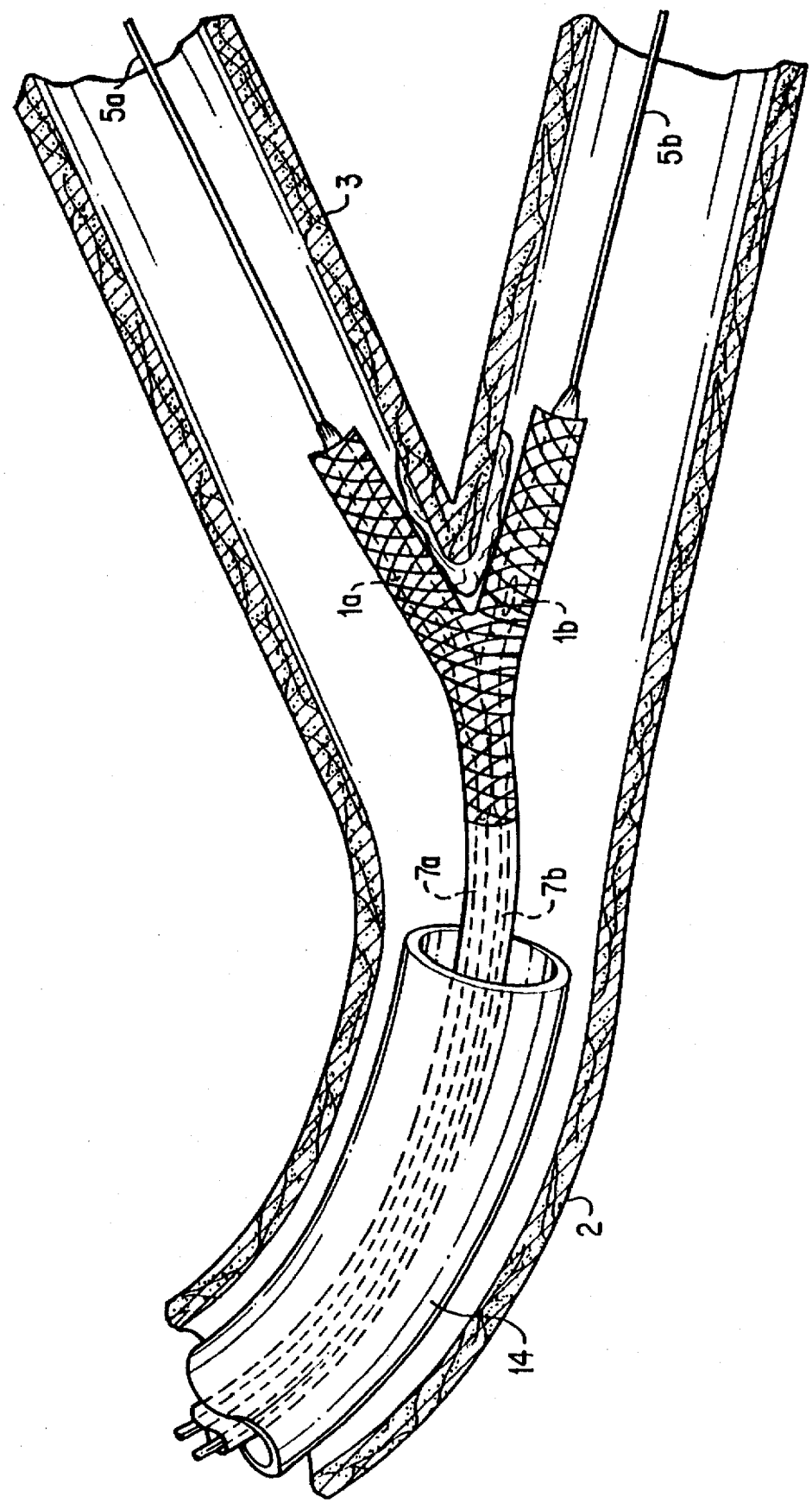

In FIG. 15, the Y-shaped deployment segment, bearing a non-self-expanding Y-shaped stent (6) mounted in compacted conformation thereon, has been advanced over the shafts of the balloon catheters (7a and 7B) to a position over the lesion (15), such that the carina of the deployment segment (11) is in apposition to the carina of the bifurcation at the origin of the side branch vessel (4). During advancement of the Y-shuttle, the balloon catheters have remained stationary. Next, as depicted in FIG. 16, the balloons (1a and 1b) are withdrawn through the arms of the Y-shaped deployment segment (10a and 10b) to lie within the deployment segment, and then inflated (FIG. 17) to deploy the stent (6) in position over the lesion (15).

Figure 18:
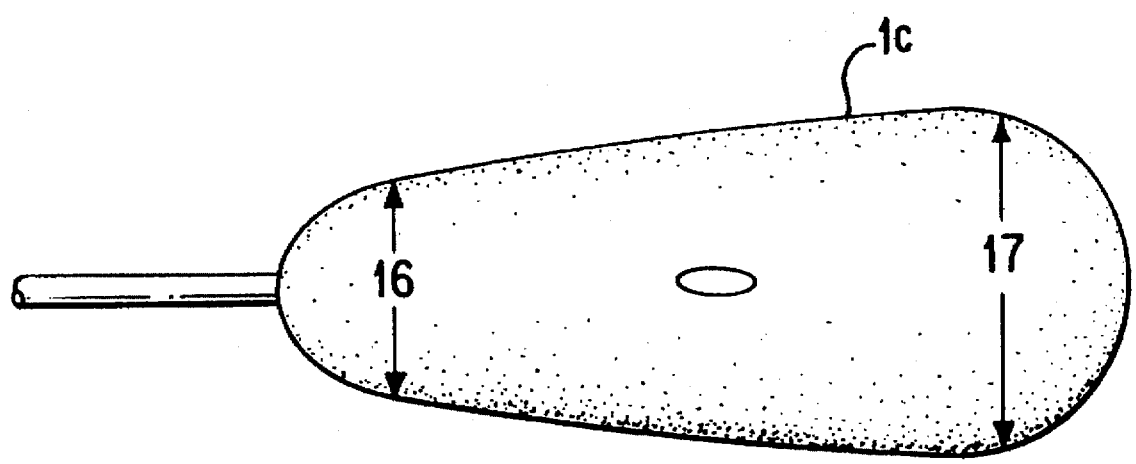
Figure 19A:
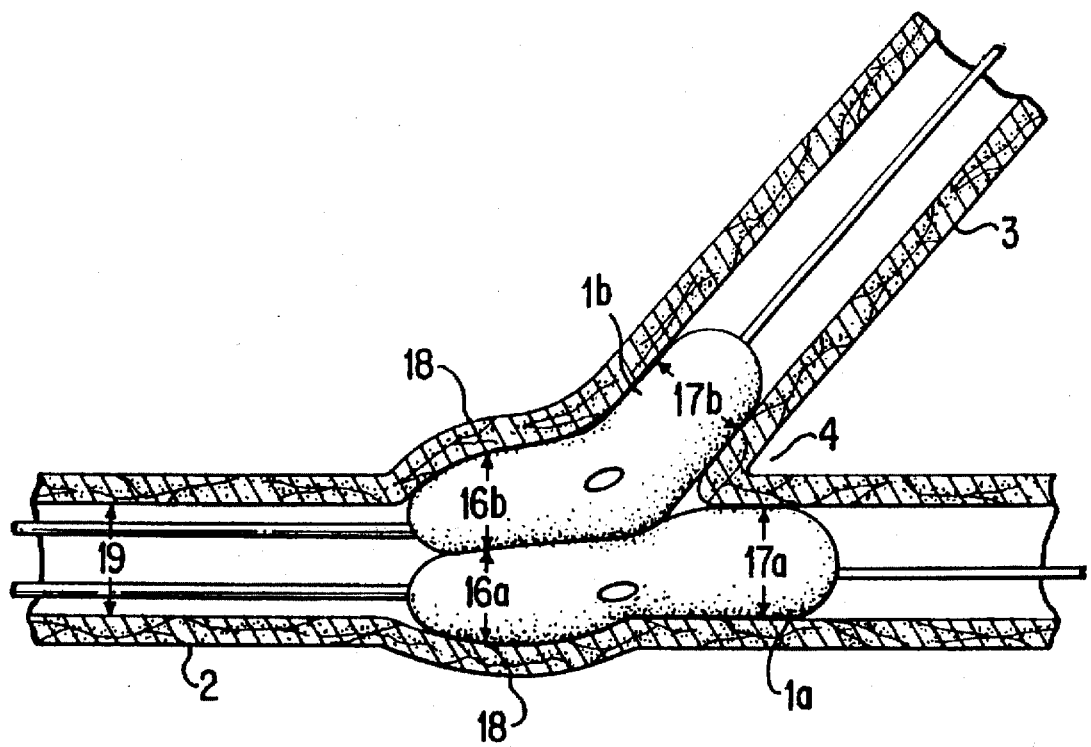
Figure 19B:
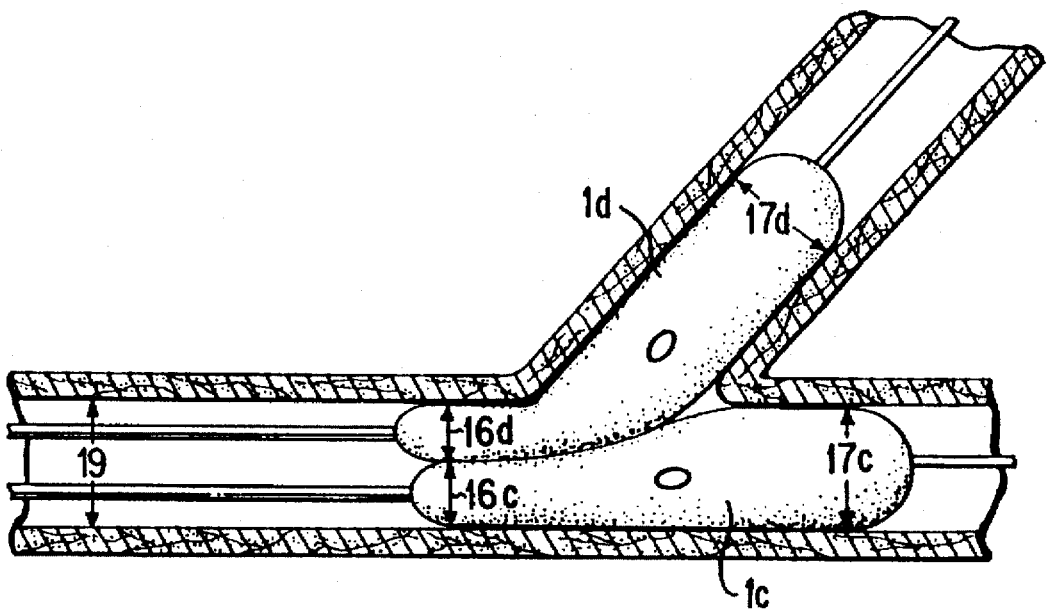

FIG. 18 depicts a reverse-tapered balloon (1c) having a proximal end (16) with a diameter which is less than the diameter of its distal end (17). The terms "proximal" and "distal" refer to the position of the balloon within the patient, wherein "proximal" refers to a direction toward the exit of the catheter from the patient, and "distal" is the opposite direction. For example, as a catheter is inserted into a patient and advanced into through a blood vessel, it is being moved distally. When the catheter is withdrawn from a patient, it is being moved proximally. An advantage of the reverse-tapered balloon is depicted in FIG. 19. FIG. 19A shows distention (18) of the main trunk vessel (2) proximal to the origin (4) of a side branch vessel (3) when conventional PTCA balloons (1a and 1b) are simultaneously inflated in a "kissing" conformation. The distal diameters (17a and 17b) of the conventional balloons fit within the main trunk vessel distal to the origin and the side branch vessel. However, the sum of the proximate diameters (16a and 16b) of the balloons exceeds the diameter of the main trunk vessel proximal to the origin (19). FIG. 19B illustrates that when reverse-tapered balloons are used (1c and 1d), the sum of the proximate diameters (16c and 16d) of the balloons is less than or equal to the diameter of the main trunk vessel (19), which, consequently, is not appreciably distended.

For purposes of clarity of description, and not by way of limitation, a further detailed description of the invention is divided into the following subsections:

(i) stents;

(ii) shuttles;

(iii) ancillary means of expansion; and (iv) methods of stent placement.

The present invention is an improvement of the invention contained in pending U.S. patent application Ser. No. 08/430,378, the entirety of which is hereby incorporated herein by reference, for use in bifurcating vessels or similar conduits, such as, but not limited to, tubular branched organs or spaces such as a proximal ureter, the junction of the common hepatic duct and the cystic duct to form the common bile duct, or a branched bronchus or trachea.

5.1. Stents

Stents which may be delivered according to the invention include any vascular or non-vascular stent intended to be placed within a blood vessel (e.g. an artery or vein, including but not limited to a coronary artery, a carotid artery, the aorta and vena cava) or similar structure.

Vascular stents which may be used according to the invention include but are not limited to PALMAZ-SCHATZ, Gianturco-Roubin, Strecker, Wiktor, Wallsten and Cordis stents. Stents which may be delivered according to the invention are not limited as to the design, material, length or thickness of the stent, and multiple contiguous or non-contiguous stents may be delivered.

In one specific embodiment, a Y-shaped stent may be utilized. Such a Y-shaped stent may preferably be hinged at the junction between the trunk and arms of the Y configuration, such that the arms of the Y shaped stent are relatively flexible and can be manipulated to fit within a bifurcating vessel where the side branch may diverge from the main trunk vessel at a variety of angles. For example, such a Y-shaped stent may be constructed by joining together two PALMAZ-SCHATZ stents by flexing and mounting an articulated two-segment PALMAZ-SCHATZ stent such that one segment of the stent extends over one arm of the shuttle and the articulating bridge extends over the external aspect of the carina of the Y-shuttle. Another PALMAZ-SCHATZ stent may then be mounted over the shaft of the Y-shuttle contiguous with the proximal edge of the segments of the bent articulated stent mounted on the arms of the Y-shuttle. A Y-stent may also be prepared, for example and not by limitation, by physically connecting individual stent segments by welding, suture, or adhesive, to name but a few means of connecting the elements.

In another nonlimiting embodiment, a Y-shaped stent may be prepared as follows. A segment of stainless steel tubing of appropriate dimensions (comparable to those currently used in the manufacture of slotted-tube stents) may be incised, over 30°–60°, with diametrically opposed arcs to form an article referred to, herein, as a prostent. A Y-shaped trocar of an appropriate size (which permits both arms of the trocar to fit into the prostent) may be placed into the prostent such that the hinge of the trocar coincides longitudinally with the incisions in the prostent. The prostent may then be heated and compressed over the trocar, so as to result in the formation of a figure-eight shaped segment over the arms of the trocar. This segment may then be divided into two tubular-shaped arms which may be connected to the more proximal shaft of the prostent over 300°–330°. A desired configuration of slots may then be etched into the two arms and the shaft of the prostent.

5.2. Shuttles

A shuttle, according to the invention, is a tubular structure having a distal and a proximal end, wherein the proximal end may preferably be kept outside of the patient (thereby allowing the operator to adjust the position of the stent during placement) and comprising a Y-shaped deployment segment (used for carrying and deploying the stent or stents) located at or near the distal end. A specific example of the distal end of such a shuttle is depicted in FIG. 12.

Figure 1:
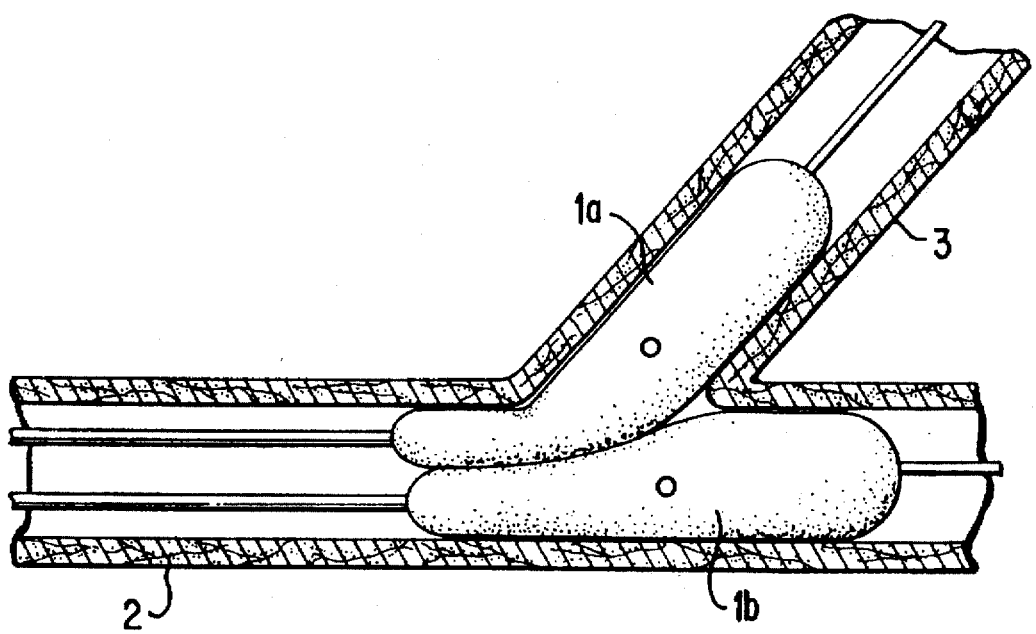
Figure 2:
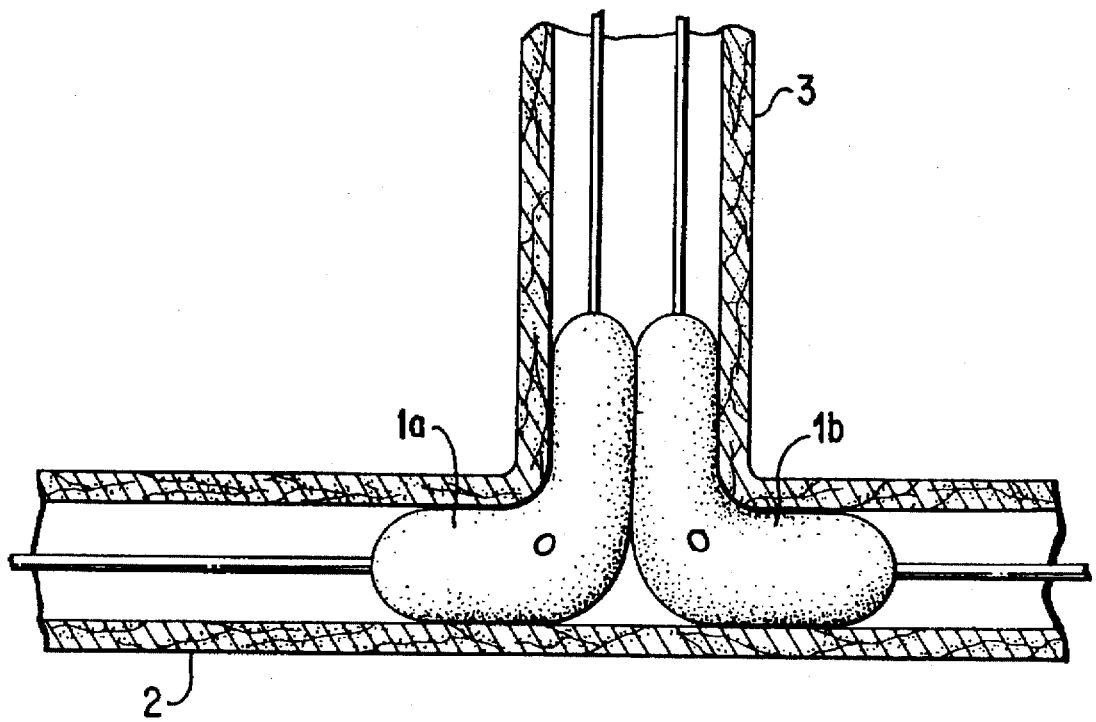
Figure 3:
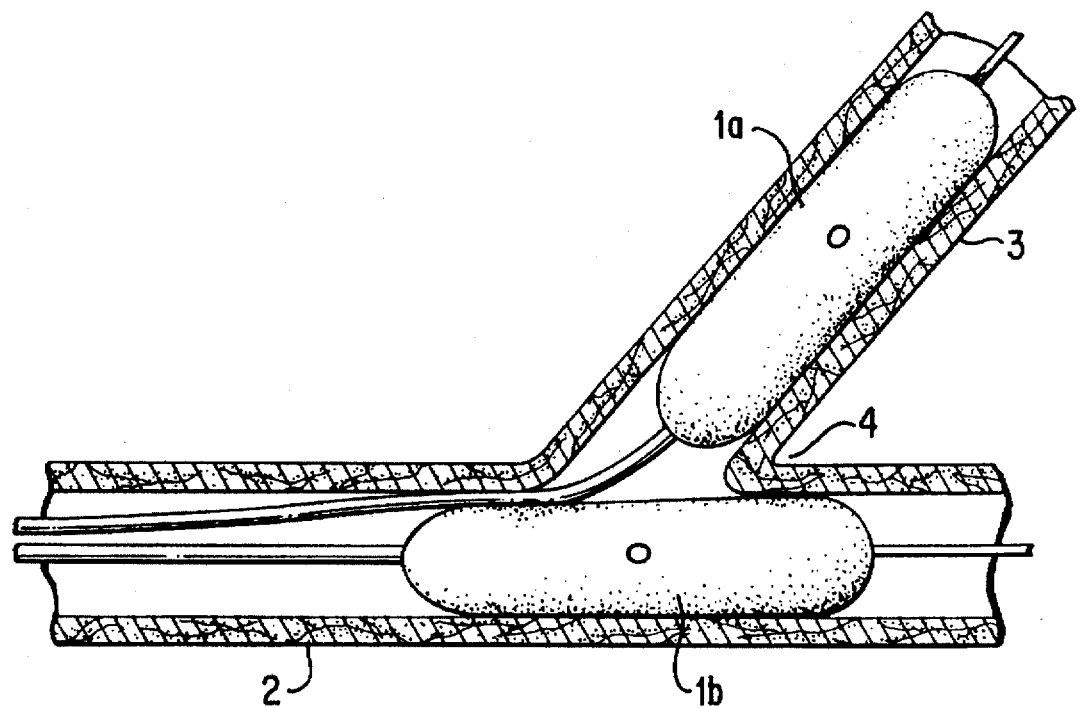
Figure 4:
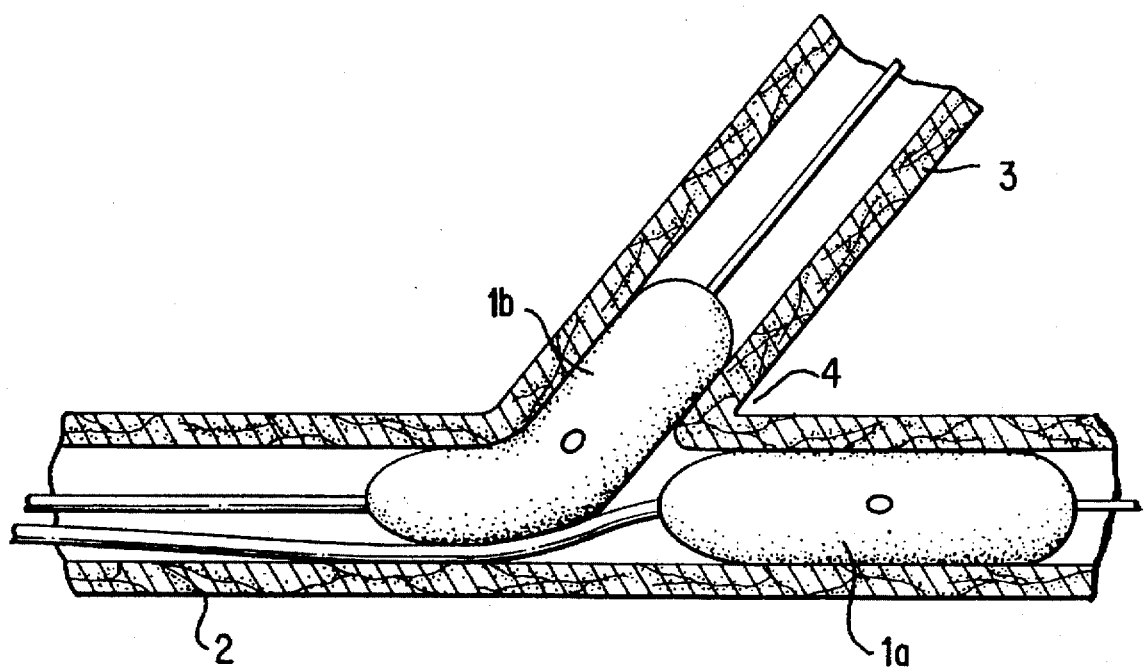
Figure 5A:
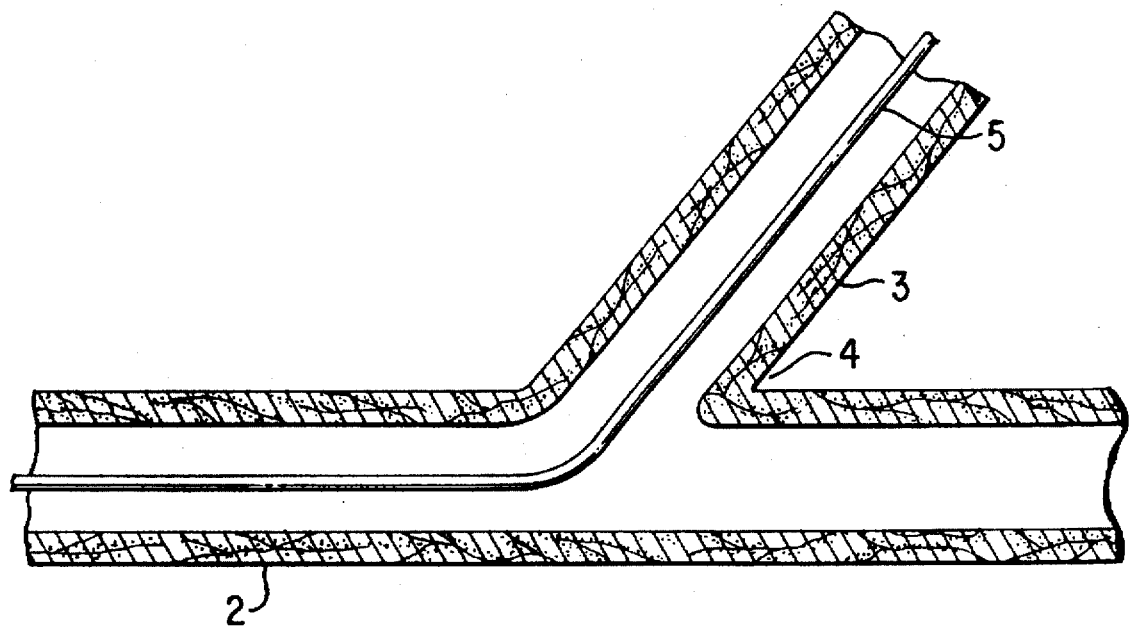
Figure 5B:
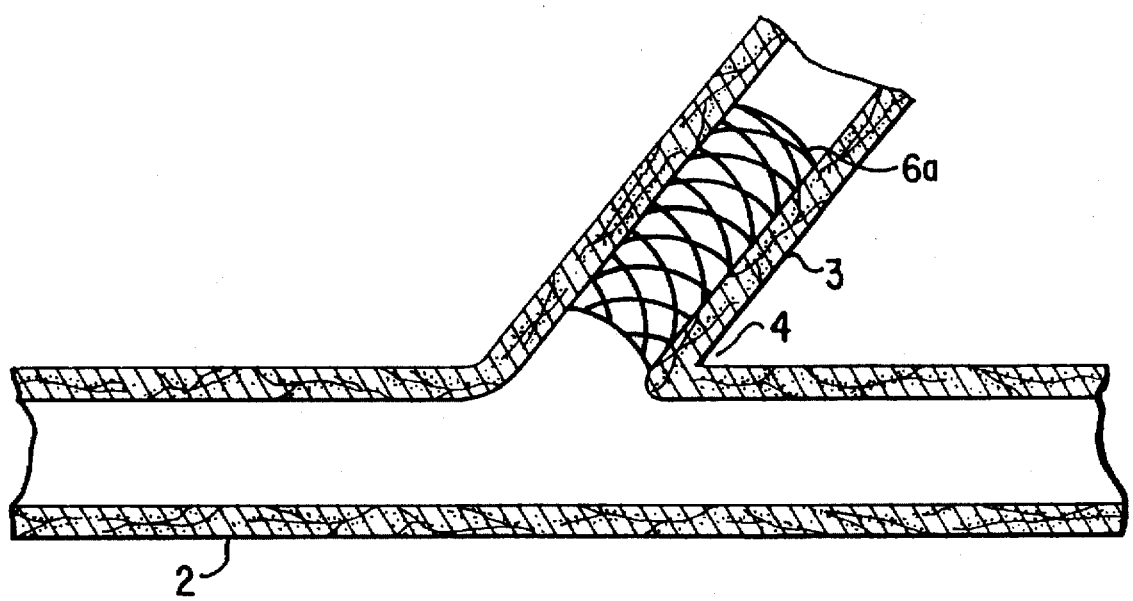
Figure 5C:
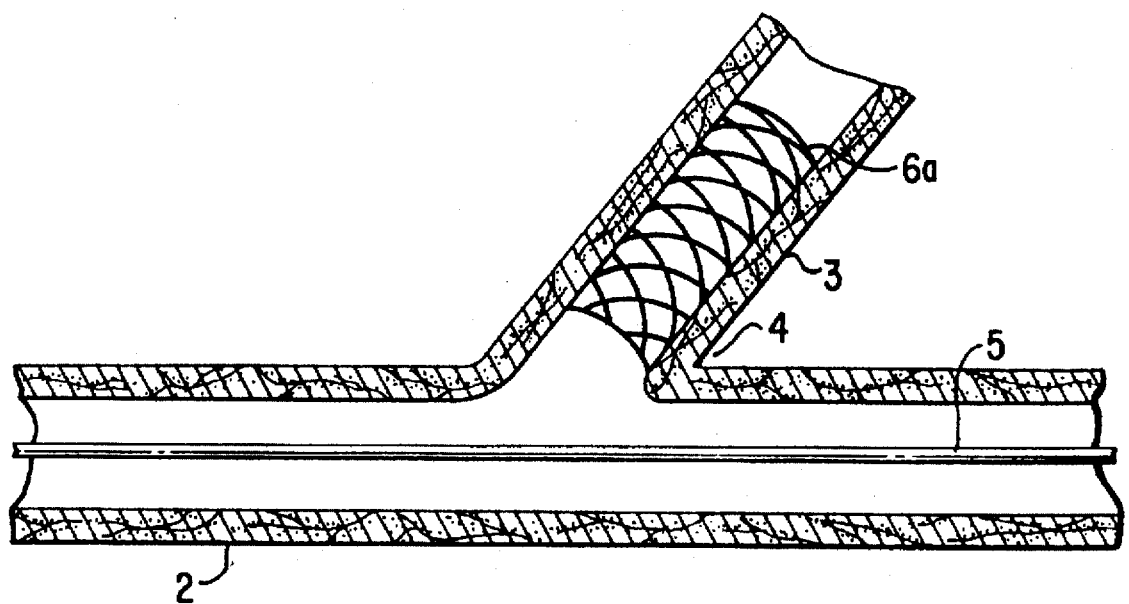
Figure 5D:
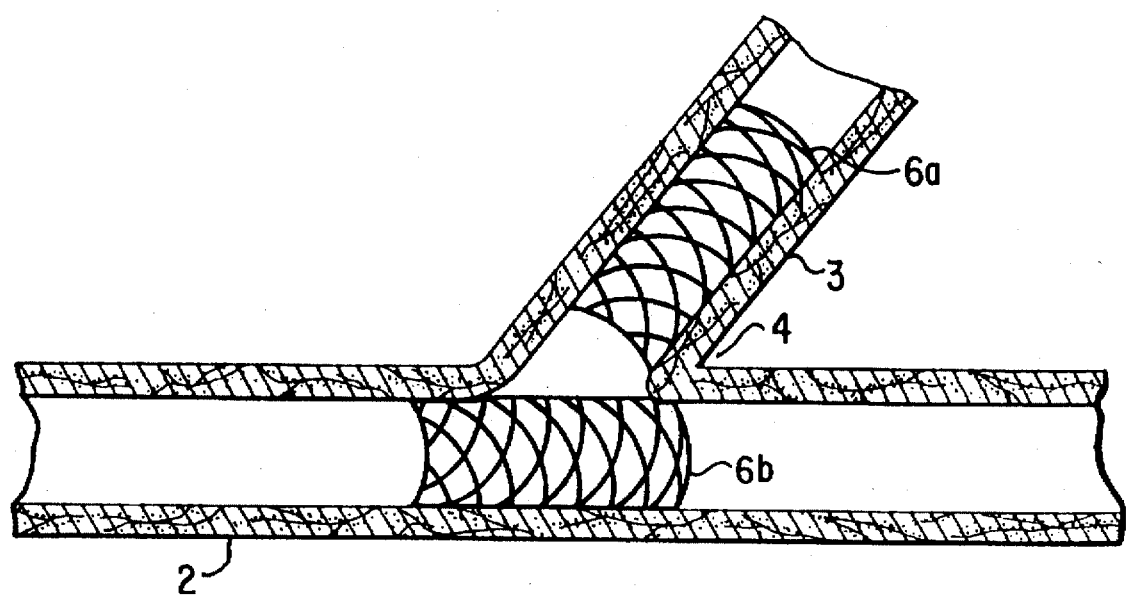
Figure 6A:
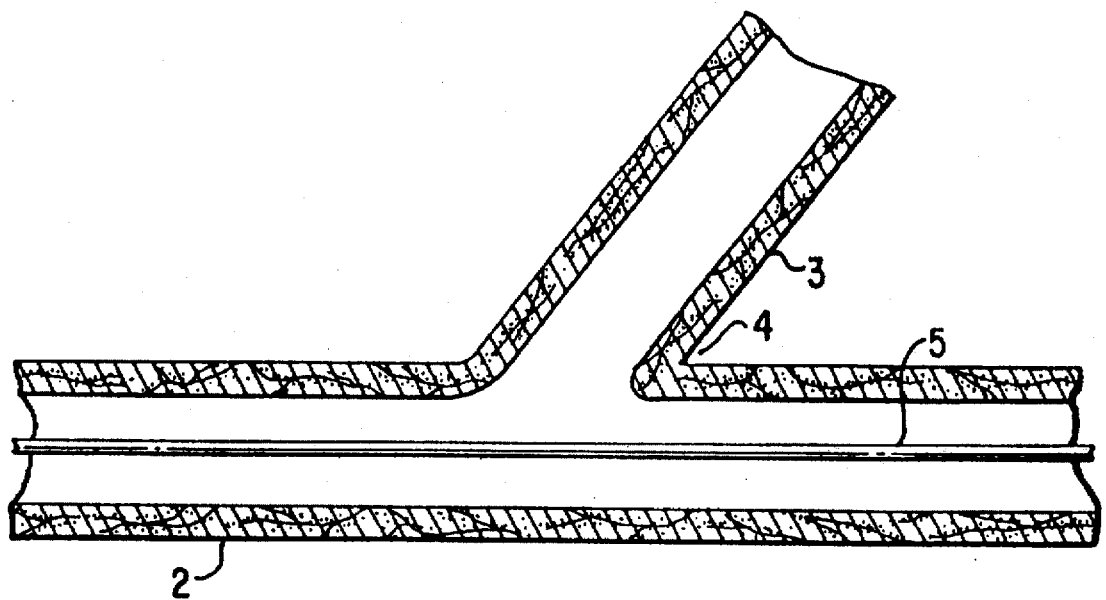
Figure 6B:
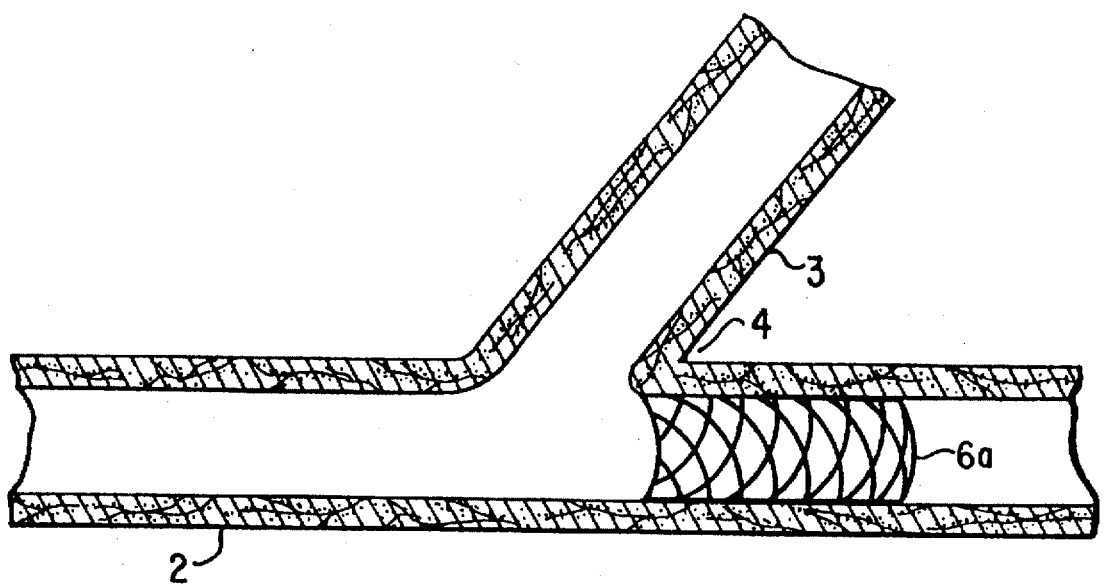
Figure 6C:
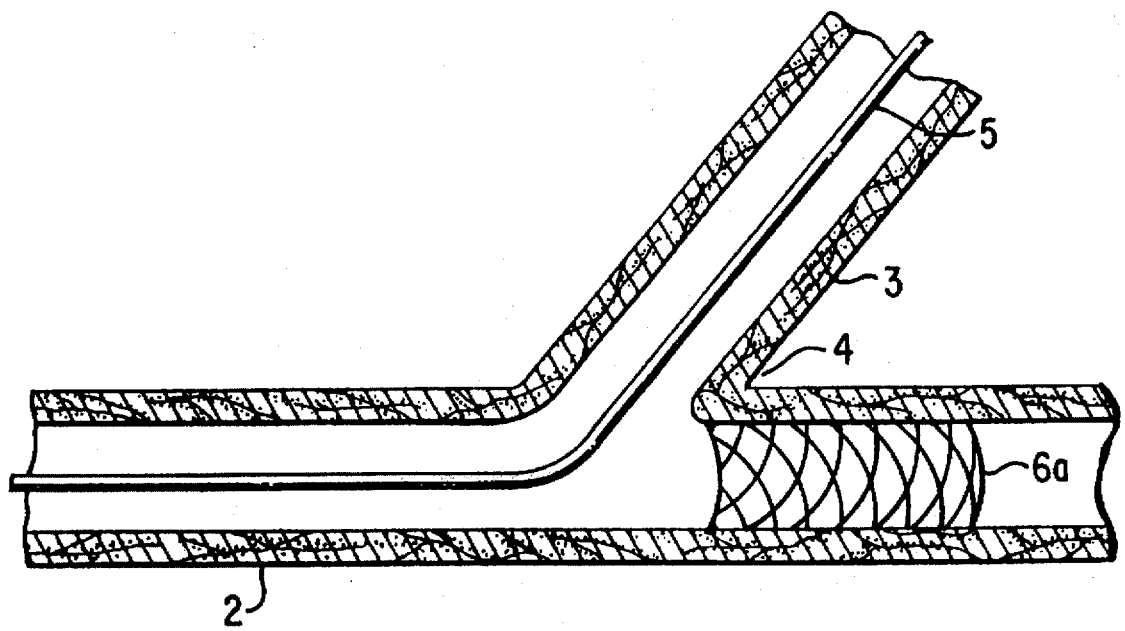
Figure 6D:
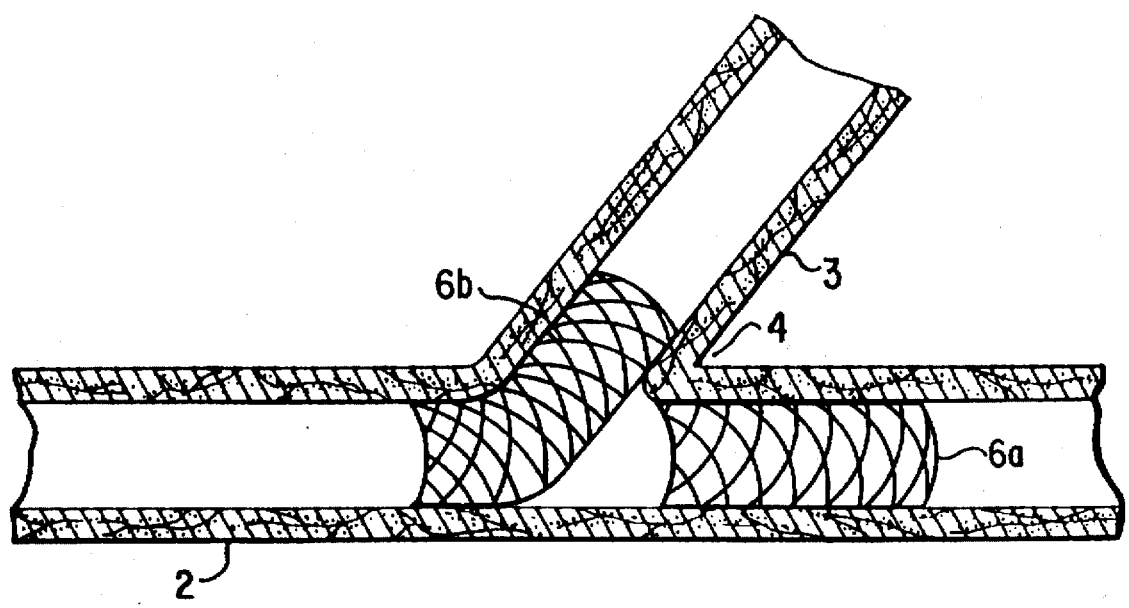
Figure 7A:
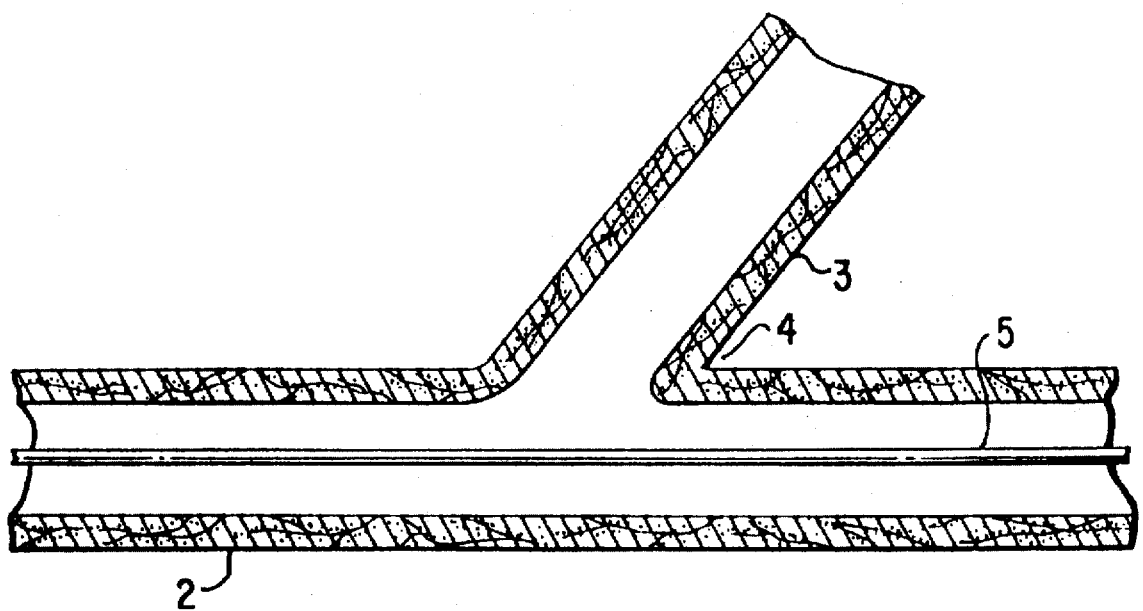
Figure 7B:
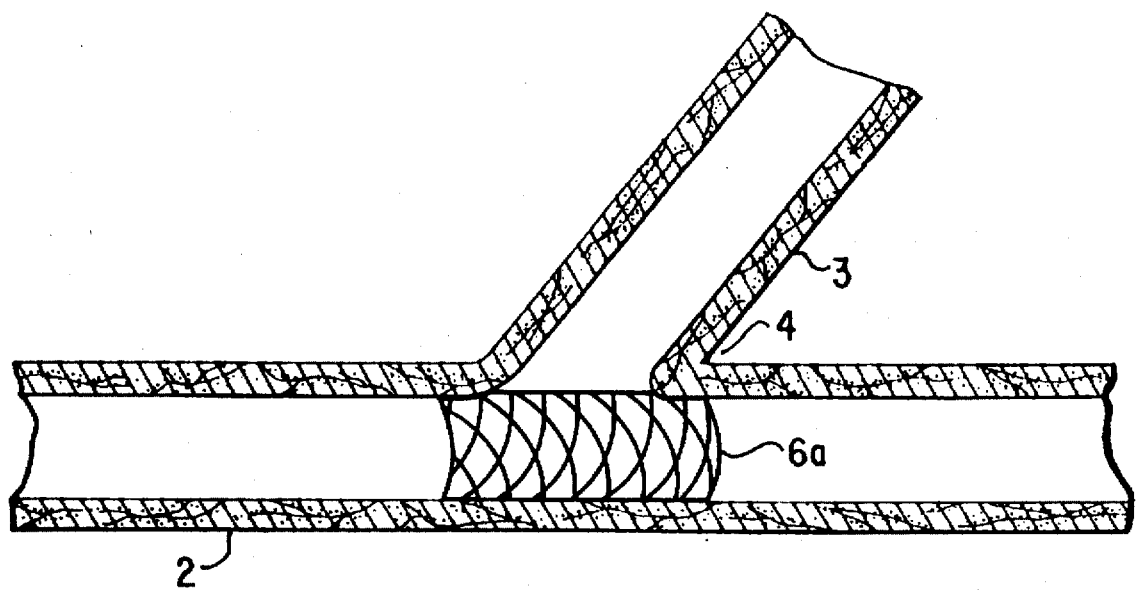
Figure 7C:
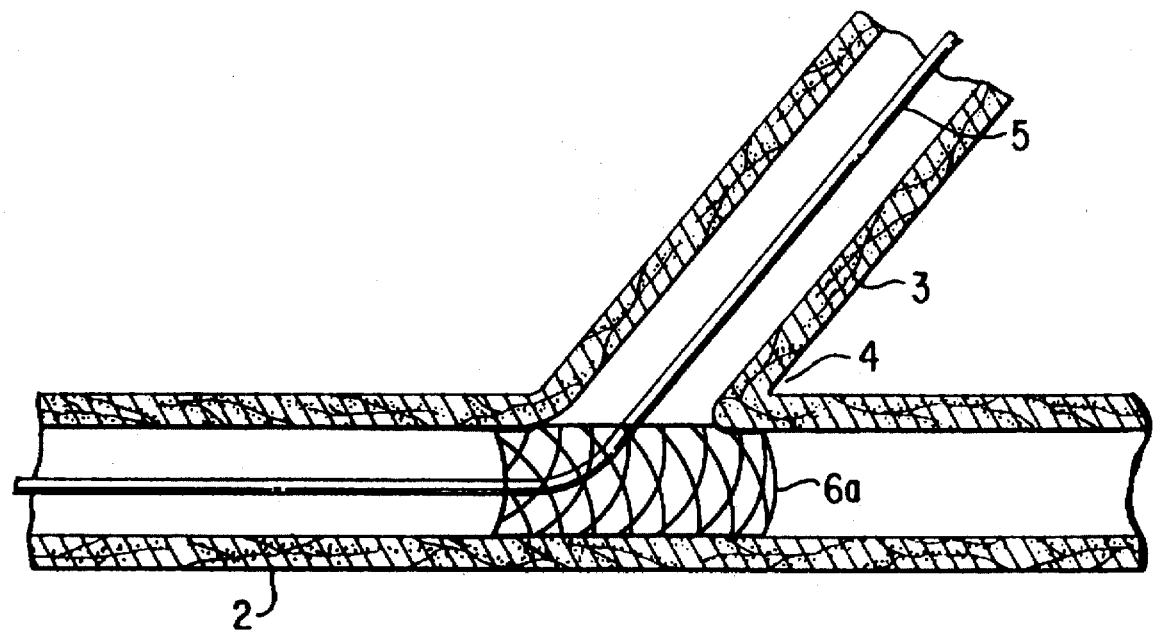
Figure 7D:
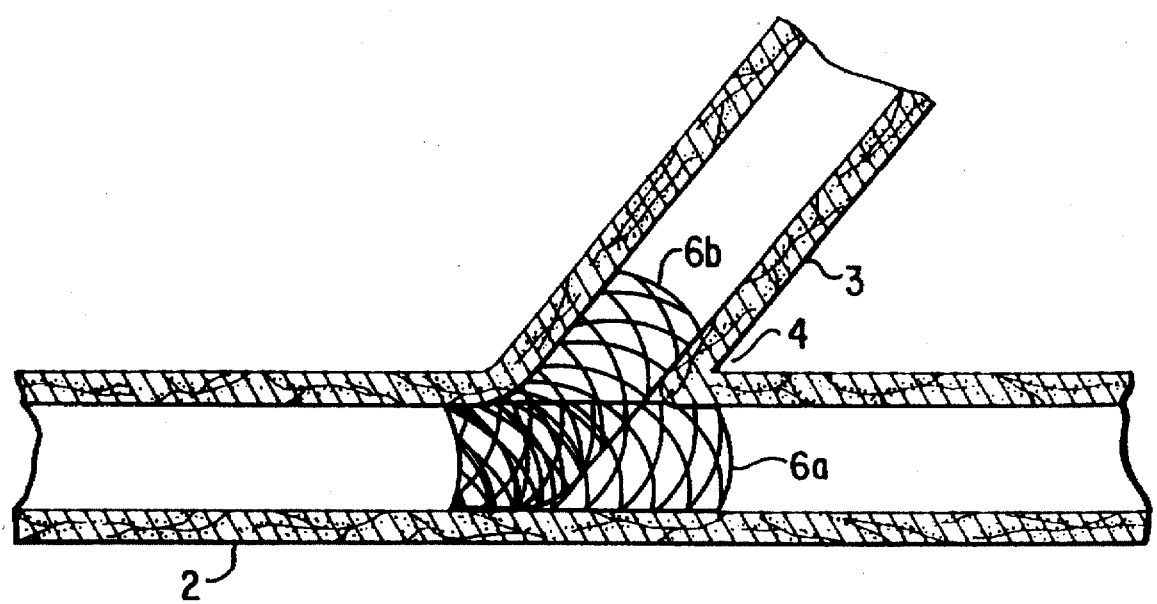
Figure 8A:
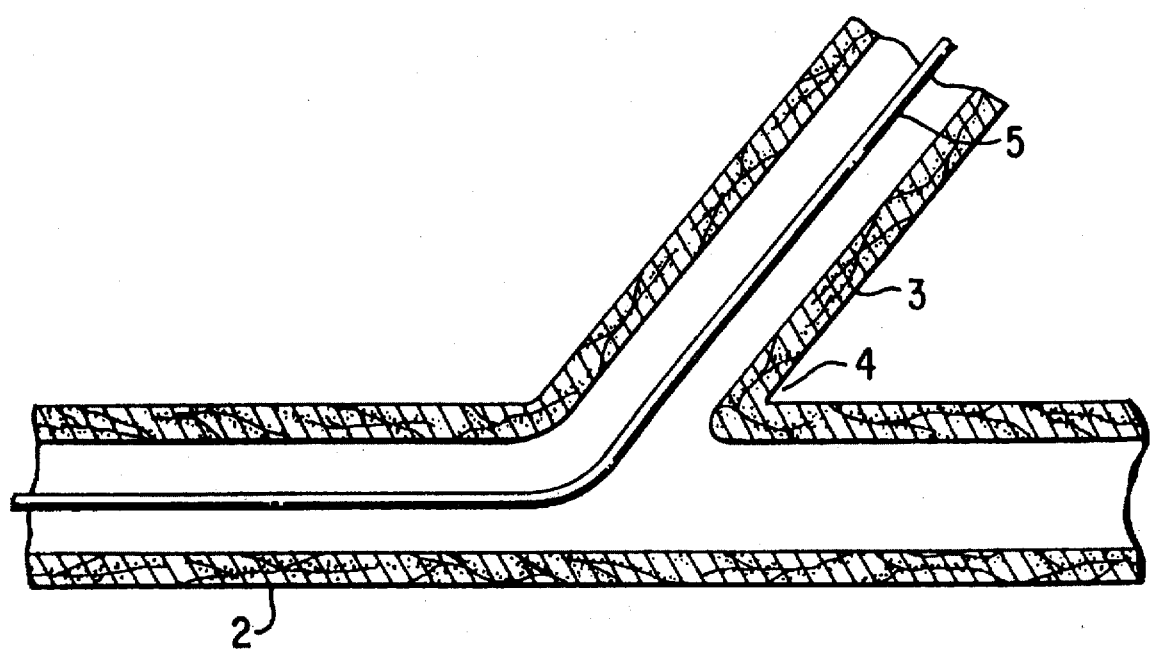
Figure 8B:
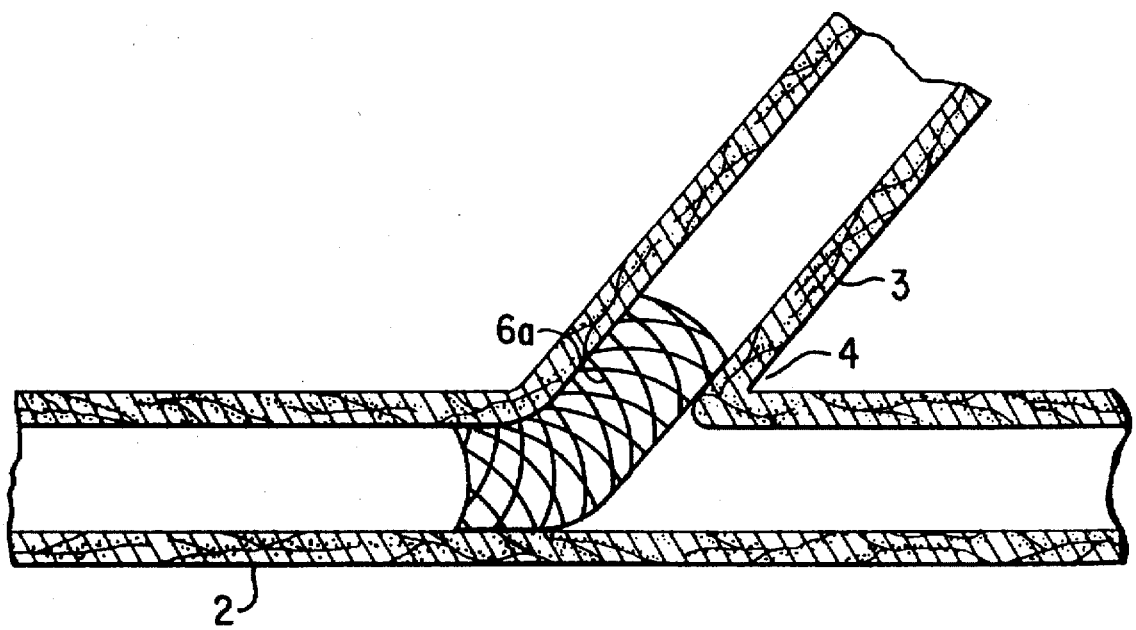
Figure 8C:
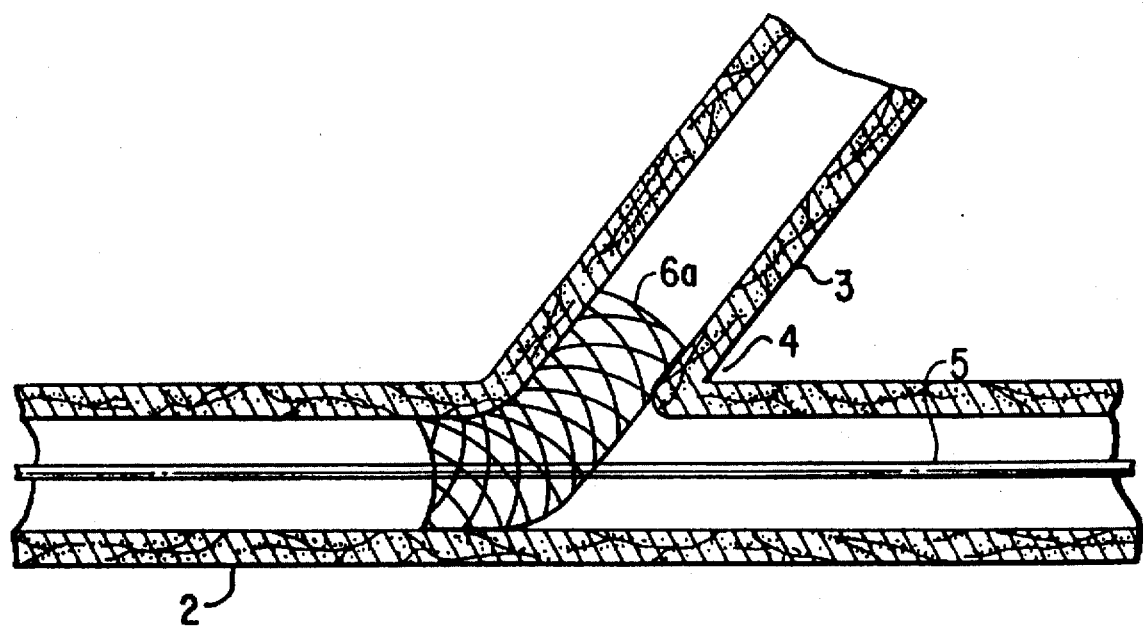
Figure 8D:
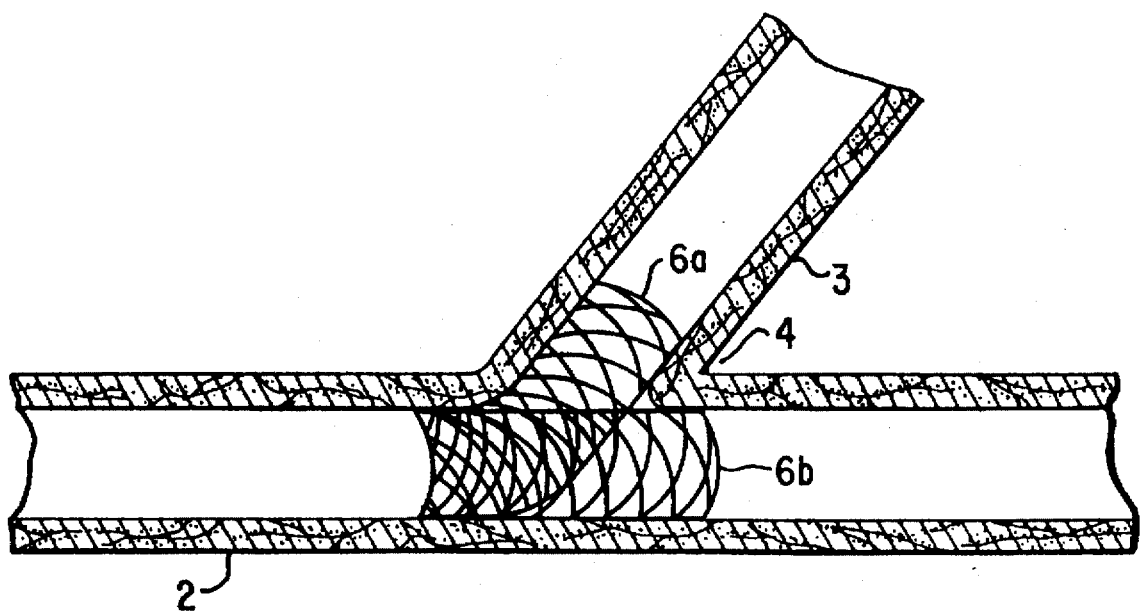
Figure 9:
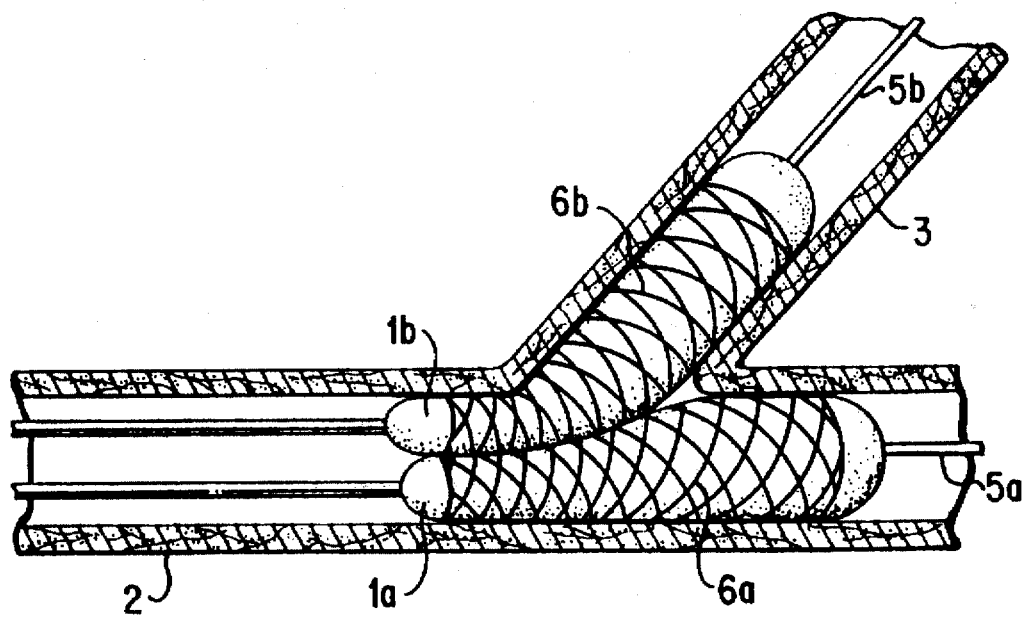
Figure 10:
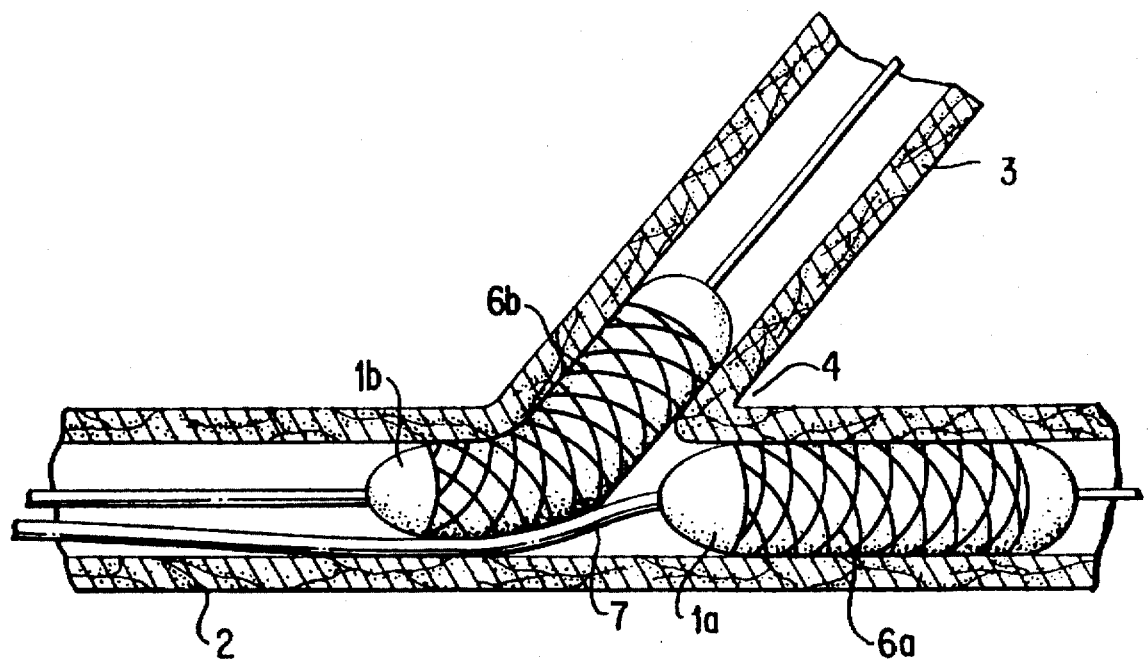
Figure 11:
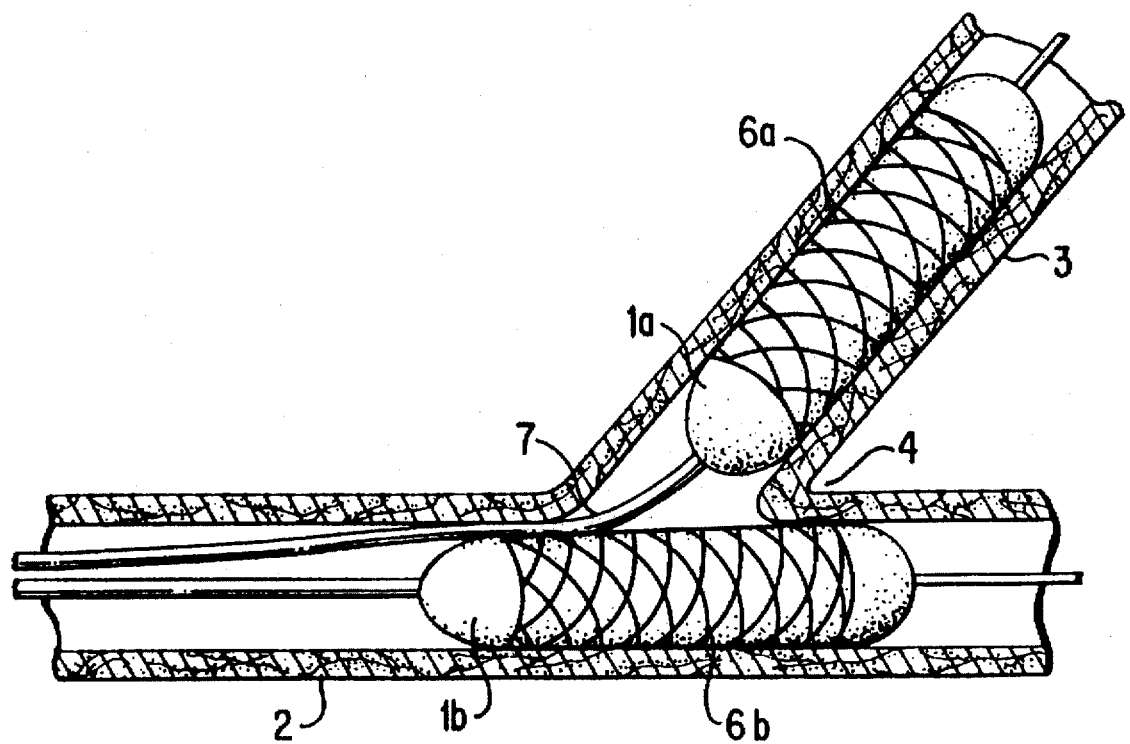
Figure 12A:
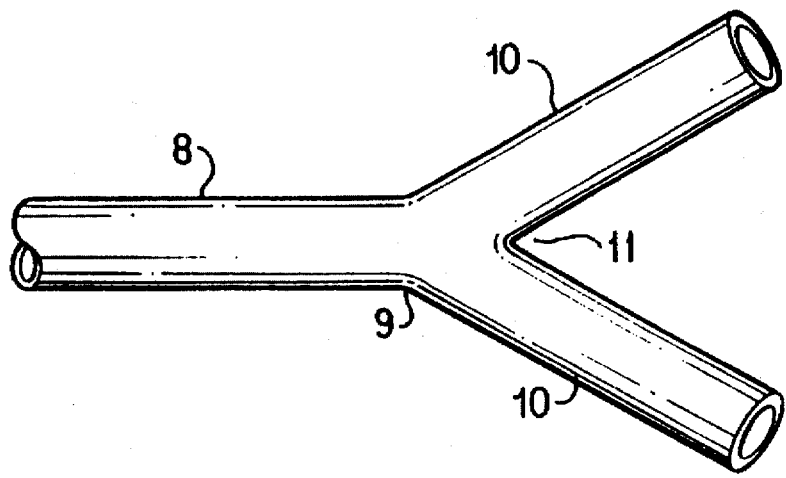
Figure 12B:
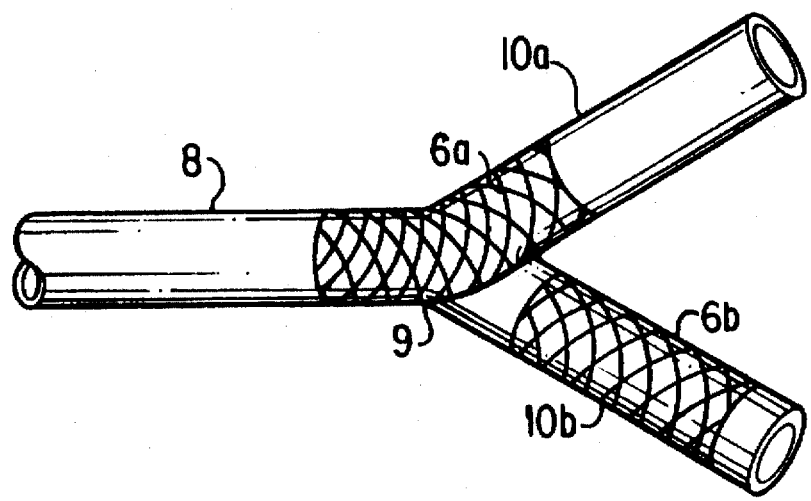
Figure 12C:
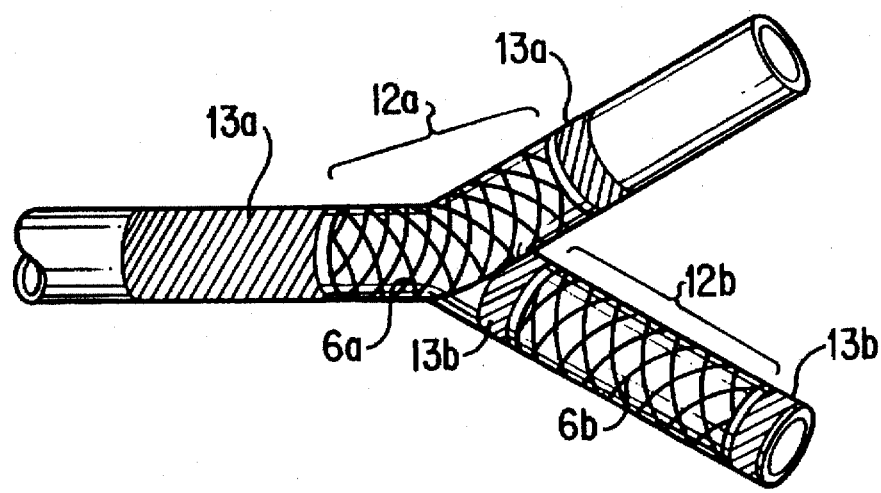
Figure 12D:
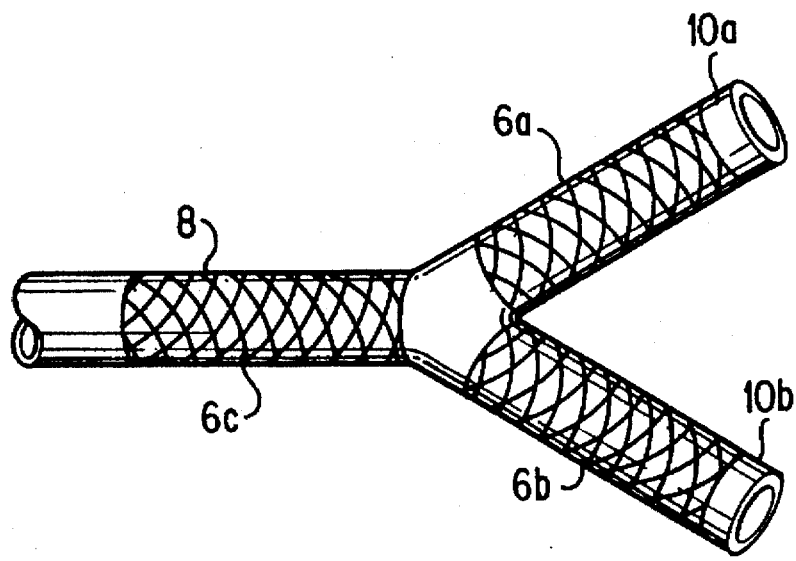
Figure 12E:
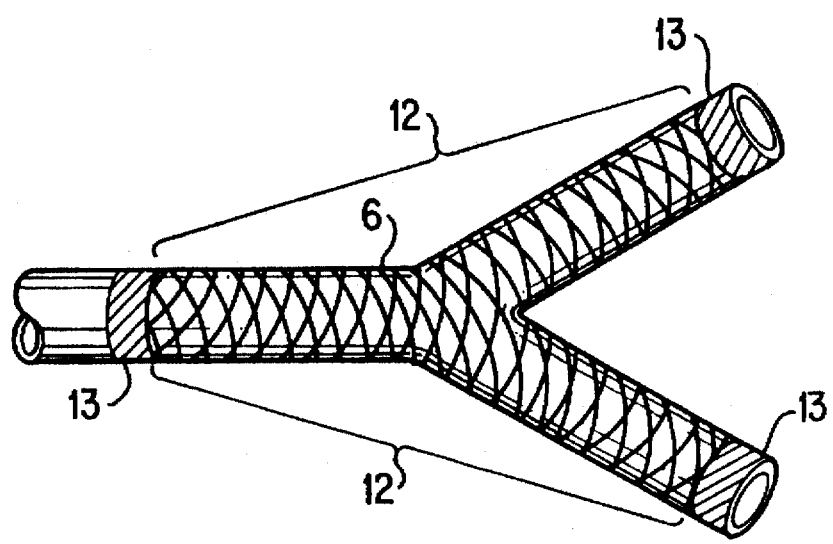
Figure 13:
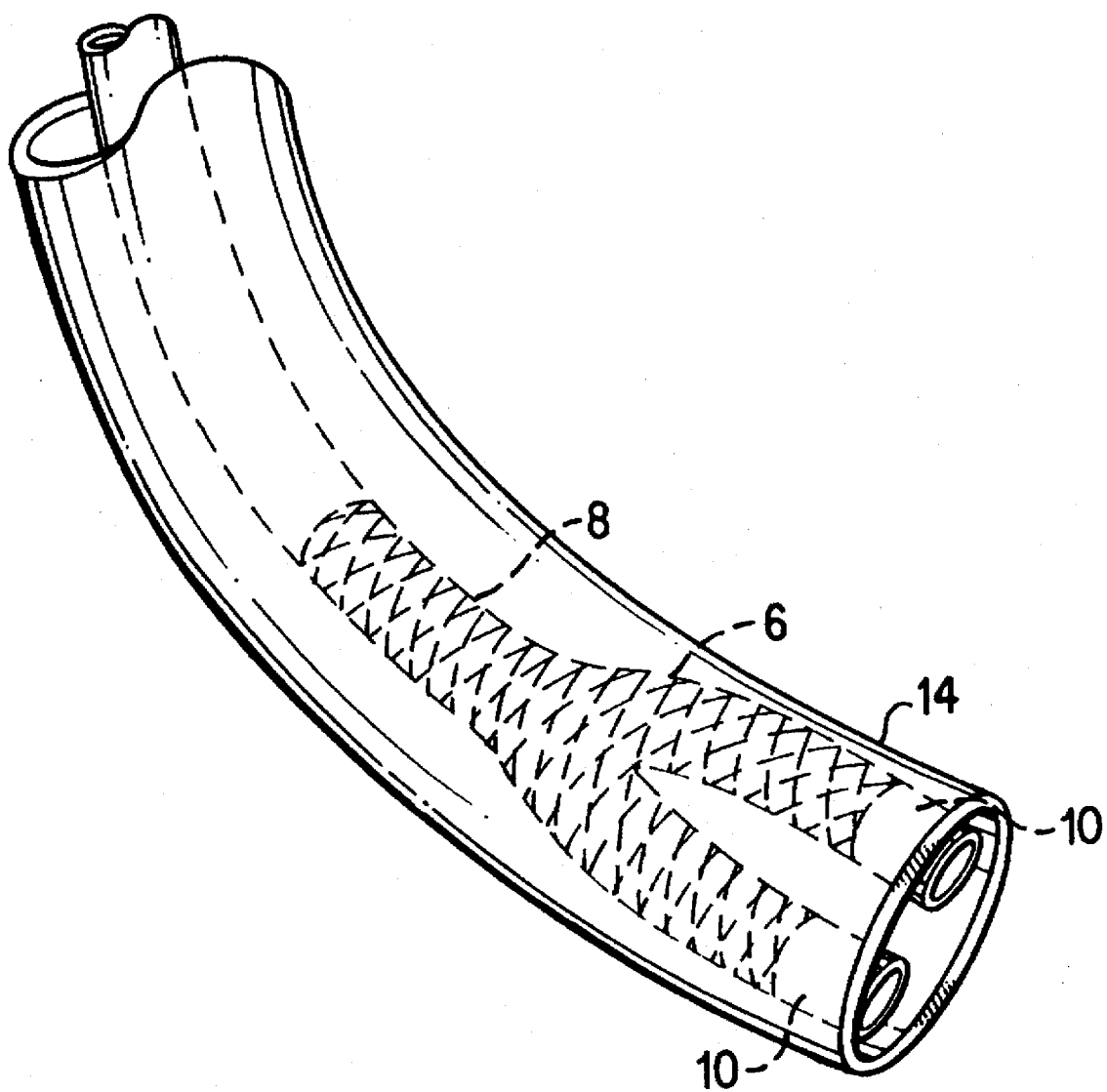
FIG. 13 depicts a Y-shuttle deployment segment within a guiding catheter (14).

The shuttle may be fabricated from a variety of materials, including, but not limited to, polyethylene, nylon, and nitinol, which are the preferred materials for the placement of stents in blood vessels. The length and radial diameter of the shuttle may vary depending upon the vessel or similar structure into which the stent is to be placed. In particular, it is important that both the unbranched portion of the catheter (hereafter referred to as the shaft), the trunk of the Y-shaped deployment segment, and both arms of the Y-shaped deployment segment, folded upward and together, fit inside the guiding catheter to be used during the procedure, which is preferably a 10 French external diameter guiding catheter (FIG. 13). Furthermore, the dimensions of the Y-shaped deployment segment should be able to accommodate the one or more balloon catheters and guide wires used in the procedure.

For example, but not by way of limitation, the approximate length of the shaft of the shuttle for placement of a stent into a coronary artery may be in the range of from 80 to 140 centimeters, and preferably from 90 to 125 centimeters, the outer radial diameter of the shaft may be in the range of from 1.0 to 2.0 millimeters, and preferably from 1.3 to 1.7 millimeters, and the inner radial diameter of the shaft may be in the range of from 0.8 to 1.6 millimeters, and preferably from 0.9 to 1.3 millimeters.

For example, but not by way of limitation, the dimensions of the Y-shaped deployment segment for use in blood vessels, including coronary vessels, may be as follows. The trunk of the Y-shaped deployment segment (see FIG. 12) may be in the range of from 3 to 20 millimeters in length, and preferably from 5 to 10 millimeters in length. The outer diameter of the trunk of the Y-shaped deployment segment may be in the range of from 1.0 to 2.5 millimeters, and preferably from 1.5 to 2.0 millimeters; and the inner diameter of the trunk of the Y-shaped deployment segment may be in the range of from 0.8 to 2.0 millimeters, and preferably from 1.0 to 1.5 millimeters. An arm of the Y-shaped deployment segment may be in the range of from 3 to 20 millimeters in length, and preferably from 5 to 10 millimeters in length. The outer diameter of an arm of the Y-shaped deployment segment may be in the range of from 0.8 to 1.5 millimeters, and preferably from 1.1 to 1.3 millimeters; and the inner diameter of an arm of the Y-shaped deployment segment may be in the range of from 0.7 to 1.4 millimeters, and preferably from 1.0 to 1.2 millimeters. It is not essential that both arms of the Y-shaped deployment segment be of the same length and/or inner or outer diameter. The trunk and arms of the Y-shaped deployment segment may each have different dimensions.

In specific, preferred embodiments of the invention, the sum of the outer diameters of the two arms of the Y-shuttle are desirably smaller than the inner diameter of a 10F guiding catheter. The inner diameter of each of the arms of the Y-shuttle is desirably large enough to accomodate a collapsed balloon pulled back into the shuttle (see below).

The Y-shaped deployment segment of the shuttle comprises one or more expandable portions, onto which one or more stents may be mounted (e.g., compacted) prior to placement in a patient, and regions flanking the expandable portion(s) (called "flanks") on the trunk and both arms which are not expandable or are less expandable than the expandable portion. The expandable portion(s) may reside in a part or parts of the trunk and both arms of the Y-shaped deployment segment, or may be located in one or both arms and/or the trunk in any combination. Several expandable portions, interrupted by less expandable flanks, may be incorporated into a single Y-shaped deployment segment. It is preferable to restrict expandable portions to areas on which a stent is to be mounted, in order to avoid damage to the vessel wall when the shuttle is expanded. Furthermore, it may be desirable to construct the trunk portion, which is to be placed in the main trunk vessel proximal to the origin of the side branch vessel, from a less expandable material in order to protect that segment of the main trunk vessel from the adverse effects of simultaneous expansion of overlapping balloons.

For conventional stents in use for treatment of coronary arteries, the length of an expandable portion may be, for example, and not by way of limitation, in the range of from 5 to 35 millimeters, and preferably from 9 to 30 millimeters. If a Y-shaped stent is to be used, the expandable portion may also be Y-shaped.

The expandable portion and flanks may be fabricated of different materials, having different expandabilities. Alternatively, the expandable portion may be made of the same material as the remainder of the shuttle, and the flanks may be created by placing two short tubular portions of reinforcing material at the boundaries of the expandable portion, or by other means known in the art.

Markers, for example radiopaque markers such as gold, tantalum or platinum markers may be placed at the distal ends of the arms and the base of the trunk of the Y-shaped deployment segment, and/or at the boundaries between an expandable portion and its flanks or between the flanks and the remainder of the shuttle to aid in stent positioning.

One or more stent may be compacted onto the expandable portion or portions of the Y-shaped deployment segment prior to placement in the patient. For non-self-expanding stents, such as, for example, a PALMAZ-SCHATZ stent, the stent may simply be crimped onto an expandable portion of the deployment segment. For self-expanding stents, the stent may be retained in non-expanded form on the shuttle by a restraining mechanism. For example, constraining sleeves may extend over both edges of the stent, retaining it in place until the sleeves are pulled apart by expansion of the expandable portion of the deployment segment. In the case of self-expanding or non-self expanding stents, the shuttle may optionally comprise a protective sheath which may cover the stent prior to deployment; such a sheath may be removed by retracting it by pulling on its proximal end, which may be kept outside of the patient at all times.

In certain, nonlimiting embodiments of the invention, biological, pharmaceutical, and/or structural materials may be incorporated into the Y-shaped deployment segment of the shuttle, such that these materials may be released upon expansion of the deployment segment by an ancillary means. For example, such materials may be incorporated into thin-walled vacuoles near the surface of the deployment segment closest to the wall of the vessel or similar structure into which the stent is to be placed, such that the vacuoles may rupture, releasing their contents, when the deployment segment is expanded. As another example, a biodegradable polymer layer with antithrombotic and/or antiproliferative properties may be incorporated into the stent delivery catheter either over the mounted stent or between the stent and the expandable portion of the deployment segment. When the deployment segment and the stent are expanded, this layer may be released from the shuttle while remaining attached to the stent in the treatment site. Materials which may be incorporated into the deployment segment include, but are not limited to, anticoagulants such as heparin, hirudin, hirulog, or platelet receptor inhibitors, thrombolytic agents such as tissue plasminogen activator, compounds that deter the proliferation of vascular smooth muscle cells (thereby decreasing the likelihood of restenosis) such as radioactive compounds, anti-CD41 antibodies or antisense oligodeoxynucleotides, radiopaque materials such as iodine or barium salts, structural materials such as fibrin layers, endothelial cells, segments of veins or arteries or synthetic grafts such as dacron. It should be noted that incorporation of such materials into the deployment segment, with consequent local release at the site of stent placement, may decrease or eliminate the need for systemic administration of such agents or other adjunct therapies. For example, the need for aggressive systemic anti-coagulation may be decreased, thereby diminishing the likelihood of hemorrhagic complications at the vascular access site.

In particular, nonlimiting embodiments of the invention, the distal tips of the arms of the Y-shaped deployment segment may be designed so as to facilitate withdrawal of an ancillary means of expansion such as a balloon into the deployment segment, for example subsequent to pre-dilatation. In alternative embodiments, the distal tips of the arms of the Y-shaped deployment segment may be either of a fixed or of an alterable configuration. For example, to achieve an alterable configuration, the distal tips may be constructed of a thermal memory alloy, such as nitinol. Such nitinol tips may be maintained at a small radial diameter to facilitate passage into a vessel or similar structure. Following pre-dilatation, for example with a balloon catheter, when it is necessary to withdraw the deflated balloon into the arm of the Y-shaped deployment segment of the shuttle, the configuration of the nitinol tip may be altered, for example, using a weak electrical current, to assume a funnel shape that may better accommodate withdrawal of the balloon. Termination of the current may then restore the initial shape of the distal tip.

In further nonlimiting embodiments of the invention, the shuttle may comprise, at the distal tips of the arms of the Y-shaped deployment segment, a structure or structures capable of forming one or more embolic filter, with fenestrations large enough to permit the passage of blood or other fluid, but small enough to trap debris (such as fragments of thrombus or atherosclerotic plaque) freed during pre-dilatation or stent deployment. The filter may be capable of fitting over, for example, a balloon catheter shaft or guidewire, and may be capable of expansion by intrinsic or ancillary means. For example, an intrinsic means of expansion would include a filter constructed of a thermal memory alloy such as nitinol, which may be expanded by a weak electrical current. As an example of an ancillary means of expansion, a balloon may be used to expand the filter. In either case, the filter and distal tips of one or both arms of the Y-shaped deployment segment may desirably be constructed such that the filter may be advanced distal to the obstructed region of the vessel and expanded prior to pre-dilatation and stent deployment. The filter itself may preferably be sufficiently flexible, by virtue of the material of which it is made or its construction, to permit pull-back of the entire delivery system following stent deployment, with the filter in its expanded shape.

In a non-limiting example, an embolic filter is comprised in a separate element, wherein the filter (for example, a coiled structure) is positioned distal to the distal end of an arm of the Y-shaped deployment segment, and is connected to a small diameter shaft running through the shuttle and extending its proximal end outside of the patient, to permit manipulation by the operator (e.g. forward advancement, retention, and withdrawal). Such a filter may be particularly useful, for example, in the placement of a carotid artery stent, to diminish the risk of embolization of thrombus or plaque to the brain, which may have profound clinical consequences and has, hitherto, limited the applicability of the stent-based treatment strategy in cerebral vasculature. For placement in a partially obstructed bifurcating carotid artery, for example, the shuttle with an expandable filter at the distal tip of one or both arms of the Y-shaped deployment segment and with one or more stents attached in a compacted condition over the deployment segment of the shuttle may be coaxially mounted over the shafts of two appropriate balloon catheters outside the patient. Each unexpanded balloon may be advanced over a guidewire distal to the lesion while the shuttle is retained inside the guiding catheter. Then, using the small diameter shaft, the embolic filter or filters may be separated from the remainder of the shuttle and advanced over the shaft of one or more balloons to a position distal to the obstruction. The filter or filters may then be expanded by intrinsic or ancillary means (e.g., the balloons), wherein the expanded filter(s) may protect the brain from embolization during pre-dilatation of the treatment site and during stent deployment. While keeping the embolic filter stationary, the obstructed segment(s) may then be pre-dilated with the balloon(s). The balloon(s) may then be deflated and advanced over the guide wire distal to the treatment site. Maintaining the embolic filter in its location, the shuttle may then be positioned so that the expandable portion(s) with the stent(s) mounted on it (them) is in the desired location. While the positions of the shuttle and the filter are maintained, the balloon catheter(s) may then be pulled back into the expandable segment and inflated, thereby deploying the stent(s). Following balloon deflation, the shuttle-balloon catheter assembly with the filter(s) in expanded conformation may be pulled out of the carotid artery into the descending aorta and out of the patient. Relatively small fragments of plaque and/or thrombus released during the procedure and trapped in the filter(s) may thus be removed out of the patient or may embolize into the systemic arterial circulation with much less grave clinical sequelae.

In a specific non-limiting embodiment of the invention, such an embolic filter may have an alterable configuration; for example, the filter may be constructed of nitinol, and have a first conformation which is a straight wire. Upon the passage of electrical current, this straight wire may assume a second conformation which is an inverted conical spiral of preset maximal diameter.

For stent placement, the Y-shaped deployment segment of the delivery catheter may be placed over the shaft of an ancillary means of expansion, such as a balloon catheter, or over the shafts of two such catheters (see below). This may be advantageous, as the delivery of stents may be improved (relative to placement over a guide wire) by the use of more rigid and larger diameter shafts as guiderails for advancing the Y-shaped deployment segment assembly into the desired position. The shuttle may be coaxial with the ancillary means of expansion over the entire length (termed an "over the catheter shuttle") or over the distal segment of the shuttle comprising the Y-shaped deployment segment (termed a "monorail shuttle") of the ancillary means of expansion.

5.3. Ancillary Means of Expansion

The stent delivery system of the invention provides for an ancillary means of expanding the Y-shaped deployment segment of the shuttle. While means of expansion other than a balloon catheter are envisioned (such as, for example, a nitinol wire, the distal segment of which is made to become a coil of a predetermined diameter when placed within the expandable deployment segment of the shuttle and when a weak electrical current is passed through such a nitinol wire) this ancillary element will be exemplified by and referred to hereafter as a balloon catheter.

The balloon catheter may be fabricated from a variety of materials, including, but not limited to, polyethylene and nylon, which are the preferred materials for the placement of stents in blood vessels.

As described above with relation to the shuttle, the length and radial diameter of the balloon catheter may vary depending upon the vessel or similar structure into which the stent is to be placed. For example, the approximate length of the shaft of a balloon catheter for placement of a stent into a coronary artery may be in the range of from 80 to 140 centimeters, and preferably from 90 to 125 centimeters, and the radial diameter of the shaft portion may be in the range of from 0.8 to 1.6 millimeters, and preferably from 0.9 to 1.3 millimeters.

The balloon portion of the balloon catheter may desirably be structured such that the balloon is capable of repeatedly and reliably advancing in unexpanded condition as well as in collapsed condition through the entire length of the shuttle, and in and out of the distal ends of the shuttle. For example, in order to achieve these goals, the balloon may preferably be a non-compliant high-pressure balloon with longer tapered ends and a smaller refolded diameter. Such a balloon may have an exaggerated gradual gentle shoulder, wherein the change from the diameter of the balloon shaft adjacent to the balloon membrane (to which the balloon membrane is tethered) to the diameter of the fully expanded balloon takes place over a relatively long distance. Upon deflation, such a balloon, even if it is a high-pressure balloon, may preferably collapse with its edges re-wrapped snugly on the shaft without heaping up. Most preferably, such a balloon maintains the diameter of the collapsed balloon (which consists of the collapsed balloon membrane and tapered catheter shaft) smaller than the more proximal shaft of the catheter.

In a preferred embodiment of the invention, the balloon is a "reverse-tapered" balloon, as depicted, for example, in FIG. 18. Such a reverse-tapered balloon, when placed in a patient, has a proximal diameter which is smaller than its distal diameter. This design facilitates the use of two balloons, in a "kissing" conformation, to simultaneously expand both arms of the Y-shaped deployment segment, in that the diameters of the distal ends of the balloons located in the arms of the Y will be greater than the proximal ends of the balloons which may both be located in the main trunk vessel proximal to the origin (FIG. 19B). If the balloons are not reverse tapered, then expansion of both balloons simultaneously may damage the main trunk vessel if the sum of the diameters of the distal ends of the balloons is too great (FIG. 19A). As an alternative or in addition to the use of a reverse tapered balloon, the trunk portion of the Y-shaped deployment segment may be rendered less expandable than the arms, for example by being fabricated from a polymer which is less elastic, or by the incorporation of elements that limit expansion.

In an alternative embodiment, the balloon may be Y-shaped. In such a case, the trunk of the Y-shaped balloon may permit the passage of two guide wires, and each arm of the Y may permit the passage of one guide wire. Such a Y-shaped balloon may be used after the pre-dilatation step in place of the two balloons used for predilatation.

The balloon in preferably fabricated from polyethylene or nylon. In specific, nonlimiting examples, where the balloon is to be used in a delivery system for stent placement in coronary arteries, the dimensions of the balloon may be as follows. The balloon may preferably reach, in an inflated state, a diameter ranging from 2.0 to 5.0 millimeters, and more preferably from 2.5 to 4.5 millimeters, and an internal pressure of from 0 to 20 atmospheres, and more preferably from 4 to 20 atmospheres. Such a balloon may preferably have a rated burst pressure of from 12 to 20 atmospheres. If the balloon is a reverse tapered balloon, in its fully inflated state the proximal diameter of the balloon may range from 1.5 to 4.0 millimeters, and preferably from 2.0 to 3.6 millimeters; and the distal diameter of the balloon may range from 2.0 to 4.0 millimeters, and preferably from 2.5 to 4.0 millimeters.

5.4. Methods of Stent Placement

The following is a general description of a method for stent placement in a bifurcating vessel. Various modifications to this method may be required depending on the structure into which the stent is to be placed, and the needs of particular patients. The method may be used for the placement of single or multiple self-expanding or non-self-expanding stents.

First, the bifurcating vessel or similar structure for stenting may be identified, and a path for the Y-shuttle stent delivery system may be established. In the case of a blood vessel, a guiding catheter and a guide wire may be inserted, wherein the guiding catheter has an internal diameter large enough to accommodate two balloon catheters and the Y-shuttle; for example, and not by way of limitation, a 10 French external diameter guide may be used. The lesion(s) in the main trunk vessel and in the side branch vessel may each be crossed with separate guide wires compatible with the balloons to be used in the procedure, without intertwining the wires. For example, but not by way of limitation, the guide wires may be 0.014" or 0.018" in diameter.

Then, a Y-shuttle with at least one expandable stent mechanically or by other means attached onto the deployment segment in contracted condition may be loaded, in retrograde fashion coaxially over the shaft of two balloon catheters outside the patient in either over-the-catheter or monorail manner depending on the type of shuttle embodiment, such that both balloons traverse the trunk of the Y-shaped deployment segment and one balloon extends into each arm of the shuttle. The balloons should be selected so that the distal end diameters are appropriate for the diameters of the main trunk vessel and side branch vessel; the sum of their distal diameters should be appropriate for the diameter of the main trunk vessel proximal to the origin of the side branch vessel.

For example, but not by way of limitation, the sum of the proximal diameters of the two balloons may desirably be equal to or no more than 25% greater than the diameter of the target vessel just proximal to the bifurcation, and the distal diameter of each balloon may be equal to or no more than 15% greater than the diameter of the corresponding branch (side branch or continuation of the main trunk distal to the bifurcation).

Next, the assembly comprising the Y-shuttle and the balloon catheters may be inserted into the guiding catheter over the guide wires.

Where an embolic filter or filters are to be used, a filter, in a collapsed state, may be advanced out of the guiding catheter distal to the lesion(s) while the remainder of the shuttle is retained inside the guiding catheter by the application of traction on the proximal ends of the shuttle kept outside the patient. The filter may then be expanded by an intrinsic or ancillary mechanism (see supra).

Next, while the Y-shuttle is retained on the shaft of the balloon catheters inside the guiding catheter by application of traction on its proximal end kept outside the patient, the balloons may be advanced, one over each guide wire, and may be positioned over the lesion or lesions within the bifurcating vessel. Meanwhile, the Y-shuttle is retained within the guiding catheter.

The balloons may then be inflated simultaneously or in an alternating manner to pressures sufficient to adequately predilate the target lesion or lesions in the main trunk vessel and the side branch vessel (FIG. 14).

The balloons may then be deflated, and then advanced to a position distal to the lesion or lesions, while the Y-shuttle remains stationary in the guide.

Of note, in certain circumstances, for example where an adequate passageway in the bifurcating vessel for the Y-shaped deployment segment of the shuttle already exists, pre-dilatation may not be necessary. In such circumstances, two unexpanded balloon catheters may be advanced distal to the lesion(s).

The stent(s), carried on the Y-shaped deployment segment of the shuttle, may then be moved into the desired position within (and preferably extending over) the lesion(s), as shown in FIG. 15, while the position of the balloon catheters in the coronary artery is maintained by application of traction on their proximal ends kept outside the patient. In moving the shuttle into this position, the carina of the shuttle may be fit within the carina of the bifurcation, at the origin of the side branch vessel. Radiopaque markers defining the location of the stent(s) may aid in stent positioning.

The deflated balloons may be withdrawn into the Y-shaped deployment segment, as shown in FIG. 16. In certain specific embodiments of the invention, this withdrawal may be facilitated by alterable distal tips of arms of the Y-shaped shuttle, for example, wherein the tips are constructed of a thermal memory alloy such as nitinol, and a weak electrical current may be used to create a wider aperture to facilitate withdrawal of the balloons.

Figure 17:
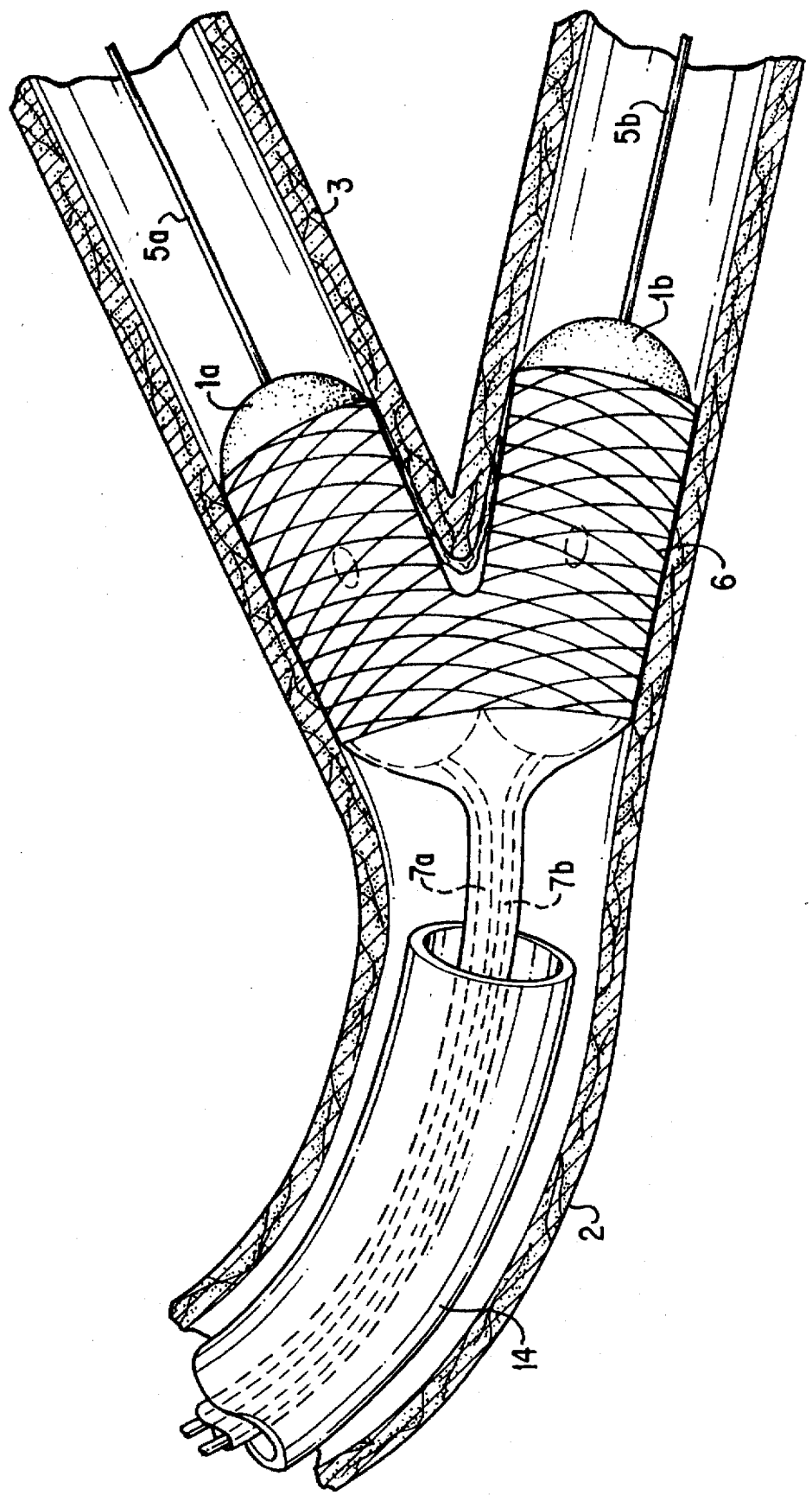

Next, the balloons may be inflated to deploy the stent or stents, as shown in FIG. 17.

Where a stent is a self-expanding stent, expansion of the deployment segment creates a structural change that releases the constrained stent; for example, central expansion may release the stent from peripherally located sleeves which overlap the edges of the stent. In specific, nonlimiting embodiments of the invention, pharmaceutical substances may be released by expansion of the deployment segment.

Following deployment, the balloons may be deflated, and the entire Y-shuttle stent delivery assembly, including balloon catheters, may be withdrawn from the patient.

Various publications are cited herein, which are hereby incorporated by reference in their entireties.

What is claimed is:

1. A stent delivery system comprising
   (a) a shuttle for delivering one or more stents in a bifurcating vessel in a patient in need of such treatment comprising a tubular catheter having, at or near its distal end, a Y-shaped deployment segment having an expandable portion;
   (b) a stent mounted on the expandable portion of the Y-shaped deployment segment of the shuttle; and
   (c) two balloon catheters, each having a shaft and each comprising a balloon at its distal end;
   wherein the Y-shaped deployment segment of the shuttle may be passed over the shafts of the balloon catheters and its expandable portion may be expanded by inflation of the balloons to deliver the stent in a desired location in a bifurcating vessel in the patient.

2. A method for placing a stent in a bifurcating vessel of a patient wherein the bifurcating vessel contains one or more lesions, comprising
   (i) introducing two balloon catheters, each having a shaft and each comprising a balloon at its distal end, into the bifurcating vessel such that the both balloons are within the one or more lesions;
   (ii) inflating the balloons so as to dilate the one or more lesions;
   (iii) deflating the balloons;
   (iv) advancing the balloons distal to the one or more lesions;
   (v) passing a shuttle, comprising a tubular catheter having at or near its distal end a Y-shaped deployment segment having an expandable portion, wherein a stent is mounted on the expandable portion of the deployment segment, over the shafts of the balloon catheters, such that the stent is positioned within the dilated one or more lesions;
   (vi) withdrawing the deflated balloons into the shuttle such that the balloons lie within the Y-shaped deployment segment;
   (vii) inflating the balloons, thereby expanding the expandable portion of the Y-shaped deployment segment and delivering the stent within the dilated one or more lesions;
   (viii) deflating the balloons; and
   (ix) withdrawing the shuttle and the balloon catheters from the patient.

3. The method of claim 2, wherein more than one stent is mounted on the Y-shaped deployment segment and delivered.

4. The method of claim 2, wherein the stent is a Y-shaped stent.

* * * * *